(12) United States Patent
Chen et al.

(10) Patent No.: US 11,946,083 B2
(45) Date of Patent: Apr. 2, 2024

(54) METHOD FOR THE MICROBIAL PRODUCTION OF SPECIFIC NATURAL CAPSAICINOIDS

(71) Applicant: Conagen Inc., Bedford, MA (US)

(72) Inventors: Hui Chen, North Billerica, MA (US); Xiaodan Yu, Lexington, MA (US); LanLan Zhou, Bedford, MA (US); Hongxue Wang, Jiangsu (CN); Min Wang, Bedford, MA (US)

(73) Assignee: Conagen Inc., Bedford, MA (US)

( * ) Notice: Subject to any disclaimer, the term of this patent is extended or adjusted under 35 U.S.C. 154(b) by 36 days.

(21) Appl. No.: 17/821,810

(22) Filed: Aug. 24, 2022

(65) Prior Publication Data

US 2022/0403427 A1     Dec. 22, 2022

Related U.S. Application Data

(62) Division of application No. 16/317,844, filed as application No. PCT/US2017/042944 on Jul. 19, 2017, now Pat. No. 11,459,591.

(60) Provisional application No. 62/363,951, filed on Jul. 19, 2016.

(51) Int. Cl.
| C12P 13/02 | (2006.01) |
| A23L 27/10 | (2016.01) |
| A61K 9/00 | (2006.01) |
| C07C 233/18 | (2006.01) |
| C07C 233/20 | (2006.01) |
| C11B 9/00 | (2006.01) |

(52) U.S. Cl.
CPC ............. *C12P 13/02* (2013.01); *A23L 27/10* (2016.08); *A61K 9/0014* (2013.01); *C07C 233/18* (2013.01); *C07C 233/20* (2013.01); *C11B 9/0061* (2013.01); *C12Y 203/01086* (2013.01); *A23V 2002/00* (2013.01)

(58) Field of Classification Search
None
See application file for complete search history.

(56) References Cited

U.S. PATENT DOCUMENTS

| 4,493,848 A | 1/1985 | Lahann et al. |
| 5,094,782 A | 3/1992 | Chen et al. |
| 6,022,718 A | 2/2000 | Iwai et al. |
| 7,759,548 B2 | 7/2010 | Metz et al. |

(Continued)

FOREIGN PATENT DOCUMENTS

| CN | 103087998 A | 5/2013 |
| CN | 10/3173444 A | 6/2013 |

(Continued)

OTHER PUBLICATIONS

[No Author Listed] ThaleMine AT4G23850—Gene LACS4. Retrieved from <https://apps.araport.org/thalemine/portal.do?externalids=AT4G23850> on Apr. 1, 2018.

(Continued)

*Primary Examiner* — Erin M. Bowers
(74) *Attorney, Agent, or Firm* — Wolf, Greenfield & Sacks, P.C.

(57) ABSTRACT

The present invention relates to the production of capsaicinoid compounds including Capsaicin and Nonivamide via microbial fermentation.

20 Claims, 8 Drawing Sheets

Specification includes a Sequence Listing.

(56) References Cited

U.S. PATENT DOCUMENTS

| | | | |
|---|---|---|---|
| 9,371,549 B2 | 6/2016 | Silverman et al. | |
| 9,951,358 B2 | 4/2018 | Chen et al. | |
| 10,392,643 B2 | 8/2019 | Chen et al. | |
| 10,655,150 B2 | 5/2020 | Chen et al. | |
| 10,793,881 B2 | 10/2020 | Chen et al. | |
| 11,459,591 B2 | 10/2022 | Chen et al. | |
| 2003/0145350 A1 | 7/2003 | Spener et al. | |
| 2003/0157670 A1 | 8/2003 | Nakanishi et al. | |
| 2004/0033530 A1 | 2/2004 | Awrey et al. | |
| 2007/0220634 A1 | 9/2007 | Metz et al. | |
| 2007/0244192 A1 | 10/2007 | Metz et al. | |
| 2007/0245431 A1 | 10/2007 | Metz et al. | |
| 2007/0261138 A1 | 11/2007 | Graham et al. | |
| 2008/0213413 A1 | 9/2008 | Ito et al. | |
| 2010/0152291 A1 | 6/2010 | Amino et al. | |
| 2010/0256413 A1 | 10/2010 | González Molinillo et al. | |
| 2011/0166371 A1 | 7/2011 | Kisaka et al. | |
| 2013/0005003 A1 | 1/2013 | Roessler et al. | |
| 2013/0029387 A1 | 1/2013 | Nikolau et al. | |
| 2014/0248668 A1 | 9/2014 | Raghavan et al. | |
| 2014/0371477 A1 | 12/2014 | Wood et al. | |
| 2016/0138061 A1 | 5/2016 | Haas et al. | |
| 2016/0168603 A1 | 6/2016 | Garg et al. | |
| 2016/0273014 A1 | 9/2016 | Chen et al. | |
| 2016/0340701 A1 | 11/2016 | Chen et al. | |
| 2017/0247733 A2 | 8/2017 | Chen et al. | |
| 2019/0010522 A1 | 1/2019 | Chen et al. | |
| 2019/0390231 A1 | 12/2019 | Chen et al. | |
| 2021/0317485 A1 | 10/2021 | Chen et al. | |

FOREIGN PATENT DOCUMENTS

| | | | |
|---|---|---|---|
| CN | 103725652 A | 4/2014 | |
| IN | 402 009 A1 | 10/2009 | |
| JP | 2003-210164 A | 7/2003 | |
| JP | 2008-514221 A | 5/2008 | |
| JP | 2013-116104 A | 6/2013 | |
| WO | WO 1998/00557 A2 | 1/1998 | |
| WO | WO 2003/087321 A2 | 10/2003 | |
| WO | WO 2006/100680 A2 | 9/2006 | |
| WO | WO 2008/034648 A1 | 3/2008 | |
| WO | WO 2009/157376 A1 | 12/2009 | |
| WO | WO 2013/006953 A1 | 1/2013 | |
| WO | WO 2013/021261 A2 | 2/2014 | |
| WO | WO 2015/066615 A1 | 5/2015 | |
| WO | WO 2015/066722 A1 | 5/2015 | |
| WO | WO 2015/109168 | * 7/2015 | |
| WO | WO 2015/109168 A1 | 7/2015 | |
| WO | WO 2015/160842 A1 | 10/2015 | |
| WO | WO 2018/017772 A1 | 1/2018 | |
| WO | WO 2018/119343 A1 | 6/2018 | |

OTHER PUBLICATIONS

[No Author Listed], Invitrogen S.O.C. Medium Catalog No. 15544-034. 2002. 1 page.
Ashrafi et al., De novo assembly of the pepper transcriptome (*Capsicum annuum*): a benchmark for in silico discovery of SNPs, SSRs and candidate genes. BMC Genomics. Oct. 30, 2012;13(571):1-15.
Aza-González et al., Molecular biology of capsaicinoid biosynthesis in chili pepper (*Capsicum* spp.). Plant Cell Rep. May 2011;30(5):695-706.
Batchelor et al., Determination of the Scoville Heat Value for Hot Sauces and Chilies: An HPLC Experiment. J Chem Educ. 2000; 77(2):266.
Belza et al., Bioactive food stimulants of sympathetic activity: effect on 24-h energy expenditure and fat oxidation. Eur J Clin Nutr. Jun. 2005;59(6):733-41.
Bosland et al., 'Bhut Jolokia'—The World's Hottest Known Chile Pepper is a Putative Naturally Occurring Interspecific Hybrid. HortScience. Apr. 2007; 42(2):222-224.
Catchpole et al., Extraction of chili, black pepper, and ginger with near-critical $CO_2$, propane, and dimethyl ether: analysis of the extracts by quantitative nuclear magnetic resonance. J Agric Food Chem. Aug. 13, 2003;51(17):4853-60.
Caterina et al., The capsaicin receptor: a heat-activated ion channel in the pain pathway. Nature. Oct. 23, 1997;389(6653):816-24.
Constant et al., Nonivamide, a Constituent of Capsicum oleoresin. J Nat Pro. 1996;59(4):425-426.
Crombie et al., Amides of vegetable origin. Part VI. Synthesis of capsaicin. J Chem Soc. 1955:1025-1027.
Curry et al., Transcripts for possible capsaicinoid biosynthetic genes are differentially accumulated in pungent and non-pungent *Capsicum* spp. Plant Sci. Oct. 15, 1999; 148(1):47-57.
De Wulf et al., Bioconversion of vanillin to vanillyl alcohol in a two-phase reactor. Appl Biochem Biotechnol. 1989; 20:165-180.
Del Rosario Abraham-Juárez M et al., Virus-induced silencing of Comt, pAmt and Kas genes results in a reduction of capsaicinoid accumulation in chili pepper fruits. Planta. Feb. 2008;227(3):681-95. Epub Nov. 13, 2007.
Du et al., Engineering microbial factories for synthesis of value-added products. J Ind Microbiol Biotechnol. Aug. 2011;38(8):873-90.
Fujino et al., Molecular identification and characterization of two medium-chain acyl-CoA synthetases, MACS1 and the Sa gene product. J Biol Chem. Sep. 21, 2001;276(38):35961-6. Epub Jul. 24, 2001.
Garcés-Claver et al., Identification, validation and survey of a single nucleotide polymorphism (SNP) associated with pungency in *Capsicum* spp. Theor Appl Genet. Nov. 2007;115(7):907-16. Epub Sep. 19, 2007.
GenBank Accession No. JW054178.1. Sep. 1, 2012. 1 page.
Geneseq database accession No. ADL 72268. Shockey et al. Oct. 23, 2003.
Geneseq database accession No. ADL 72357. Shockey et al. Oct. 23, 2003.
Govindarajan et al., Capsicum—production, technology, chemistry, and quality. Part V. Impact on physiology, pharmacology, nutrition, and metabolism; structure, pungency, pain, and desensitization sequences. Crit Rev Food Sci Nutr. 1991;29(6):435-74. DOI: 10.1080/10408399109527536.
Häusler et al., Microbial production of natural flavours. 1997. ASM News, 63: 551-559.
Higashiguchi et al., Purification and structure determination of glucosides of capsaicin and dihydrocapsaicin from various Capsicum fruits. J Agric Food Chem. Aug. 9, 2006;54(16):5948-53.
Jordt et al., Molecular basis for species-specific sensitivity to "hot" chili peppers. Cell. Feb. 8, 2002;108(3):421-30.
Kaminaga et al., Molecular cloning and characterization of a glucosyltransferase catalyzing glucosylation of curcumin in cultured Catharanthus roseus cells. FEBS Lett. Jun. 4, 2004;567(2-3):197-202.
Kobata et al., Potent production of capsaicinoids and capsinoids by Capsicum peppers. J Agric Food Chem. Nov. 20, 2013;61(46):11127-32. doi: 10.1021/jf403553w. Epub Nov. 6, 2013.
Kometani et al., Glucosylation of Capsaicin by Cell Suspension Cultures of Coffea arabica. Biosci Biotechnol Biochem. 1993;57(12):2192-2193.
Kozik et al., CLPY5434.b1_C15.ab1 CLP(XYZ) lettuce perennis Lactuca perennis cDNA 25 clone CLPY5434, mRNA sequence. Genbank entry [online]. National Center for Biotechnolgy Information. Oct. 6, 2006, [Retrieved on Mar. 23, 2018]. Retrieved from the Internet: <URL:https://www.ncbi.nlm.nih.gov/nucest/DW094259.1 ?report=genbank>; 2 pages.
Lee et al., Molecular cloning of a novel pathogen-inducible cDNA encoding a putative acyl-CoA synthetase from *Capsicum annuum* L. Plant Mol Biol. Aug. 2001;46(6):661-71.
Mazourek et al., A dynamic interface for capsaicinoid systems biology. Plant Physiol. Aug. 2009; 150(4):1806-21.
NCBI Reference Sequence: XP 016564091.1. May 5, 2016. 1 page.
Prasad et al., Influence of 8-methyl-nonenoic acid on capsaicin biosynthesis in in-vivo and in-vitro cell cultures of *Capsicum* spp. J Agric Food Chem. Mar. 8, 2006;54(5):1854-9.

(56) References Cited

OTHER PUBLICATIONS

Prasad et al., Characterization of capsaicin synthase and identification of its gene (csy1) for pungency factor capsaicin in pepper (*Capsicum* sp.). Proc Natl Acad Sci U S A. Sep. 5, 2006;103(36):13315-20. Epub Aug. 28, 2006. Erratum in: Proc Natl Acad Sci U S A. Apr. 17, 2007;104(16):6876. Retraction in: Prasad et al., Proc Natl Acad Sci U S A. Dec. 23, 2008;105(51):20558.

Prasad et al., Valine pathway is more crucial than phenyl propanoid pathway in regulating capsaicin biosynthesis in Capsicum frutescens mill. J Agric Food Chem. Sep. 6, 2006;54(18):6660-6.

Qin et al., Whole-genome sequencing of cultivated and wild peppers provides insights into Capsicum domestication and specialization. Proc Natl Acad Sci U S A. Apr. 8, 2014;111(14):5135-40. doi: 10.1073/pnas.1400975111. Epub Mar. 3, 2014.

Ramachandra et al., Biotransformation of isoeugenol to vanilla flavour metabolites and capsaicin in suspended and immobilized cell cultures of Capsicum frutescens: study of the influence of β-cyclodextrin and fungal elicitor. Process Biochem. Nov. 1999;35(3-4):341-348.

Reilly et al., Determination of capsaicin, dihydrocapsaicin, and nonivamide in self-defense weapons by liquid chromatography-mass spectrometry and liquid chromatography-tandem mass spectrometry. J Chromatogr A. Apr. 6, 2001;912(2):259-67.

Ruan et al., Capsicum annuum cultivar Yidu-Red inbred 201 acyltransferase (Pun1) mRNA, complete cds. GenBank Accession No. GU300812.1. Dated Jan. 17, 2010. [https://www.ncbi.nlm.nih.gov/nuccore/283766072].

Shimoda et al., Glycosylation of capsaicin and 8-nordihydrocapsaicin by cultured cells of Catharanthus roseus. Phytochemistry. May 2007;68(10):1391-6. Epub Apr. 20, 2007.

Shockey et al., *Arabidopsis* contains a large superfamily of acyl-activating enzymes. Phylogenetic and biochemical analysis reveals a new class of acyl-coenzyme a synthetases. Plant Physiol. Jun. 2003;132(2):1065-76.

Shockey et al., *Arabidopsis* contains nine long-chain acyl-coenzyme a synthetase genes that participate in fatty acid and glycerolipid metabolism. Plant Physiol. Aug. 2002;129(4):1710-22.

Simbaqueba et al., Development and characterization of microsatellite markers for the Cape gooseberry Physalis peruviana. PLoS One. 2011;6(10):e26719. doi: 10.1371/journal.pone.0026719. Epub Oct. 21, 2011.

Stewart et al., Genetic control of pungency in C. chinense via the Pun1 locus. J Exp Bot. 2007;58(5):979-91. Epub Mar. 5, 2007.

Stewart et al., The Pun1 gene for pungency in pepper encodes a putative acyltransferase. Plant J. Jun. 2005;42(5):675-88.

Sudhakar Johnson et al., Biotransformation of ferulic acid and vanillylamine to capsaicin and vanillin in immobilized cell cultures of Capsicum frutescens. Plant Cell Tiss Organ Cult. Feb. 1996;44(2):117-121.

Surh et al., Capsaicin in hot chili pepper: carcinogen, co-carcinogen or anticarcinogen? Food Chem Toxicol. Mar. 1996;34(3):313-6. doi: 10.1016/0278-6915(95)00108-5.

Suzuki et al., Constituents of red pepper spices: chemistry, biochemistry, pharmacology and food science of the pungent principle of *Capsicum* species. In: The Alkaloids: Chemistry and Pharmacology, vol. 23. Academic Press, Orlando, FL, pp. 227-299.

Suzuki et al., Intracellular localization of capsaicin and its analogues, capsaicinoid, in Capsicum fruit 1. Microscopic investigation of the structure of the placenta of *Capsicum annuum* var. *annuum* cv. Karayatsubusa. Plant Cell Physiol. Aug. 1980;21(5):839-853.

Thalemine AT4G23850—Gene LACS4. Retrieved from<https://apps.araport.org/thalemine/portal.do?externalids=AT4G23850 >on Apr. 1, 2018.

Thiele et al., Chili pepper fruits: presumed precursors of fatty acids characteristic for capsaicinoids. J Agric Food Chem. Jun. 11, 2008;56(11):4219-24.

Thomas et al., Simple Method for Quantitation of Capsaicinoids in Peppers Using Capillary Gas Chromatography. J Agric Food Chem. 1998;46(7):2655-2663.

Tominaga et al., Structure and function of TRPV1. Pflugers Arch. Oct. 2005;451(1):143-50. Epub Jun. 22, 2005.

UniProt Accession No. Q58VTO "UniProtKB—Q58VTO (Q58VTO_CAPCH) Acyltransferase, 34, 35/34, 61Pun1, Capsicum chinense—protein sequence" Apr. 26, 2005 [located online Nov. 16, 2017 athttp://www.uniprot.org/uniproVQ58VTO].

UniProt Accession No. B5LAV6 "Putative Long Chain acyl-CoA synthetase" (Oct. 14, 2008) [retrieved on Nov. 13, 2017 from http://www.uniprot.org/uniprot/B5LAV6] p. 2, sequence.

UniProt Accession No. Q6F4D5 "Glycosyltransferase" (Aug. 16, 2004) [retrieved on Nov. 13, 2017 from http://www.uniprot.org/uniprot/Q6F4D5] p. 2, sequence.

Walsh et al., Phylogenetic Relationships of Capsicum (Solanaceae) Using DNA Sequences from Two Noncoding Regions: The Chloroplast atpB-rbcL Spacer Region and Nuclear waxy Introns. Int J Plant Sci. 2001; 162(6):1409-1418.

Weber et al., Biocatalytic potential of vanillin aminotransferase from Capsicum chinense. BMC Biotechnol. Apr. 9, 2014;14:25. doi: 10.1186/1472-6750-14-25.

WPI database AN 2014-K94081. Apr. 16, 2014. CN 103 725 652 A.

Yao et al., Supercritical Carbon Dioxide Extraction of Scotch Bonnet (*Capsicum annuum*) and Quantification of Capsaicin and Dihydrocapsaicin. J Agric Food Chem. 1994;42(6):1303-1305.

Zhang et al., Efficient free fatty acid production in *Escherichia coli* using plant acyl-ACP thioesterases. Metabolic Engineering. 2011; 13:713-722.

\* cited by examiner

METHOD FOR THE MICROBIAL PRODUCTION OF SPECIFIC NATURAL CAPSAICINOIDS

CROSS-REFERENCE TO RELATED APPLICATIONS

This application is a division of U.S. application Ser. No. 16/317,844, filed Jan. 15, 2019, entitled "METHOD FOR THE MICROBIAL PRODUCTION OF SPECIFIC NATURAL CAPSAICINOIDS", which is a national stage filing under 35 U.S.C. § 371 of International Patent Application No. PCT/US2017/042944, filed Jul. 19, 2017, entitled "METHOD FOR THE MICROBIAL PRODUCTION OF SPECIFIC NATURAL CAPSAICINOIDS", which claims priority to U.S. Provisional Application No. 62/363,951, filed on Jul. 19, 2016. The entire contents of these applications are incorporated herein by reference in their entirety.

REFERENCE TO AN ELECTRONIC SEQUENCE LISTING

The contents of the electronic sequence listing (C149770006U502-SEQ-ZJG.xml; Size: 14,021 bytes; and Date of Creation: Aug. 22, 2022) is herein incorporated by reference in its entirety.

INCORPORATION OF SEQUENCE LISTING

The sequence listing contained in the file named "C1497.70006WO00.txt", which was created on Jun. 27, 2016, is contemporaneously filed by electronic submission (using the United States Patent Office EFS-Web filing system) and incorporated herein by reference in its entirety.

FIELD OF THE INVENTION

The field of the invention relates to methods and processes useful in the microbial production of capsaicinoids. More specifically, in some embodiments, the current invention provides a method to produce nonivamide and other specific capsaicinoids in yields not otherwise possible in plant-based systems. The present invention provides, inter alia, a genetically modified *E. coli*. strain that has been modified to biosynthesize a desired capsaicinoid, a method of producing the genetically modified microorganism to produce the desired capsaicinoid, and a production method for the production of desirable capsaicinoid products in high yield and purity levels starting from a specific starting material.

BACKGROUND OF THE INVENTION

The present invention, in some embodiments, is directed to a method for modifying a microbial strain to produce a desirable capsaicinoid compound in high yield using a specific feeding source for the microbial production strain. Capsaicinoid compounds (including without limitation: capsaicin (CP), dihydrocapsaicin (DHCP), nonivamide (NV), etc.), are the "spicy" components of hot peppers, and may be effective for preventing a number of pathologies by promoting energy metabolism, stimulating the central nervous system and activating lipolytic enzymes. In addition, these compounds sterilize the gastrointestinal tract, improve immunity when consumed and are also effective for activating immunity and relieving fatigue.

Capsaicinoid Chemistry

"Spicyness" or pungency is a unique characteristic of hot peppers in the *Capsicum* genus that produce alkaloids called capsaicinoids. In nature, it is believed that capsaicinoids are present in plants to deter mammals from consuming their fruits and destroying seeds. Humans can sense capsaicinoids via a receptor structurally related to members of the transient receptor potential channels (or "TRP" family of ion channels). Similar to other receptors important in sensory neurons, the capsaicin receptor ("TRPV1" also referred to as the vanilloid TRP, vanilloid 1 Receptor or TRPV1) mediates the pungent odor and pain/hot sensations associated with capsaicin and piperine by reversibly losing sensitivity to capsaicin as well as other pain and heat stimuli when it is under prolonged exposure to the same stimulus (Caterina et al., 1997). This phenomenon may partially explain why humans can tolerate and even enjoy spicy foods, as pain sensors may be turned off.

Capsaicin ("C"), 8-methyl-N-vanillyl-trans-6-nonenamide, and dihydrocapsaicin ("DHCP"), 8-methyl-N-vanillynonanamide, are the two major capsaicinoids in peppers and are collectively responsible for up to 90% of the pungency of chili peppers, including ghost chilies (Garcés-Claver et al., 2007). These two compounds and the more minor capsaicinoid compounds represent important ingredients in foods and other uses consumed throughout the world (European Commission Scientific Committee on Food, 2002). Speaking generally, the capsaicin content of chili peppers ranges from 0.1 to 1% w/w (Govindarajan and Sathyanarayana 1991) and for many uses requires that methods be used to concentrate the CP and/or DHCP compounds. Due to the wide use of capsaicinoids in food, medicine and other industrial and self-defense uses, there has been an increasing demand for the production and concentration of capsaicinoid compounds.

The *Capsicum* genus includes over 20 species of peppers, from which *C. annuum, C. frutescens, C. chinense, C. baccatum*, and *C. pubescens* have been domesticated (Walsh and Hoot, 2001). There is wide genetic variation in pungency or spiciness levels across the various *Capsicum* species due to varying levels and types of capsaicinoids present. For example, the non-pungent sweet bell pepper from *C. annuum* scored 0.0 SHU (Scoville Heat Unit; a scale that indicates the amount of capsaicin), while the "Bhut Jolokia" or ghost chili is a hybrid between *C. chinense* and *C. frutescens* from Northeastern India, scored up to 1,001, 304 SHUs (Bosland and Baral, 2007).

Pure CP extracted from plants typically rates at approximately 16,000,000 Scoville units on the heat index and in this concentration can sell for over $5000 USD per gram (Batchelor, 2000). However, the content of capsaicinoids in hot peppers is generally very low and can be greatly affected by environmental and growth conditions leading to problems of sustainability and consistency.

When extracted from plants, typically solid-liquid extraction using solvents like hexane, chloroform, and ethanol are commonly employed for capsaicinoid recovery (Catchpole et al., 2003). However, solvent extraction is itself energy intensive, leads to problems of toxic waste disposal, requires extensive acreage for the plants themselves to be grown and yields a product that requires further purification for minor constituents to be recovered. Thus, new production methods are needed to reduce costs of pure capsaicin and/or other capsaicinoids and lessen the environmental impact of large scale cultivation and processing (Yao et al., 1994). Genetic manipulation of selected microbial strains has the potential to address these needed improvements and increase the selectivity, abundance and purity of desired capsaicinoid varieties.

In addition to the above, while consumers approve and actively seek natural and biological sources for food, fragrance, flavor or medicinal components they are also concerned about sourcing, consistent potency and environmentally sustainable production. Into this situation the microbial fermentation and production methods of the current invention provide, in some embodiments, compounds produced by modified microbial strains that have the capability to produce products biologically in quantities useful for a variety of industries and research while doing so in a more natural fashion than inorganic chemical synthesis.

Accordingly, a need exists for the development of a novel method of producing CP, NV and DHCP and other capsaicinoids through the development of a specific biologic pathway using modified microbial strains that can stably produce desirable capsaicin compounds. Specifically, the current invention provides, inter alia, methods to produce CP, NV and DHCP from a fermentation process in commercially relevant amounts.

SUMMARY OF THE INVENTION

The present invention encompasses improved methods of producing capsaicinoids. The current invention provides a method to produce capsaicinoids in modified microbes that comprise a cellular system, such as yeast or bacteria. Applicants have isolated the genes for an acyl-CoA synthetase ("ACS")(SEQ ID NO: 1) and capsaicin synthase ("CS") (SEQ ID NO: 2) and inserted them into a cellular system of interest, in a preferred embodiment this cellular system is in *E. coli*. These genes, when expressed, allow the production of capsaicinoids in that system. According to the current invention, in some embodiments, this system produces the CP, DHCP and NV capsaicinoids in substantial amounts.

According to the current invention, in some embodiments, a biosynthetic method of making carboxyl CoAs from medium/long-chain carboxylic acid including expressing an ACS and CS in a cellular system is provided. In some embodiments, said system requires long-chain carboxylic acids, growing the cellular system transformed by ACS and CS in a medium, and producing carboxyl CoAs. These cultures then produce certain capsaicinoids when the modified microbial strains are fed from natural precursors. Accordingly, nonanoic acid can be used as a feeding precursor and can be obtained, for example, from the oil of pelargonium or European olive (*Olea europaea*). Other feeding precursors of the current invention include octanoic acid, decanoic acid, vanillin and vanillylamine. Octanoic acid can also be used according to the current invention and is naturally found, for example, in palm and coconut oil. Decanoic acid is found in the seeds of *Cuphea* species. Natural vanillin can also be produced by microbial fermentation (Zhou and Yu, 2014). In addition, natural vanillylamine could be obtained from vanillin by pAMT (Weber et al., 2014).

The current method provides an approach for the development of a bacterial strain that is capable of producing significant volumes of capsaicinoids by genetic modification and targeted feeding of specific starting molecules that are more cost effective and easier to obtain.

In certain embodiments of the current invention, the target capsaicinoid produced is selected from the group consisting of NV, CP and DHCP.

An embodiment of the present disclosure is a biosynthetic method of developing capsaicinoids by making carboxyl CoAs from medium to long-chain carboxylic acids comprising expressing an ACS in a cellular system, feeding medium to long-chain carboxylic acids to the cellular system, growing the cellular system in a medium, and producing carboxyl CoAs.

A further embodiment is that the ACS is expressed from ACS1 cloned from ghost chili pepper. (For reference see Table 1.)

An alternative embodiment is that the ACS is expressed from *Arabidopsis* based on LCAS4 or LCAS5. In another embodiment, the ACS is expressed from ACS2 cloned from *Capsicum* spp. Further, in some embodiments, the ACS used in the invention is an ACS that shares a sequence identity of at least 66% (e.g., at least 70%, at least 80%, at least 90%, at least 95%, at least 99% or 100%) with the ACS1 cloned from ghost chili pepper. In another embodiment, the ACS is an ACS that shares a sequence similarity of at least 92% (e.g., 92%, 93%, 94%, 95%, 96%, 97%, 98%, 99% or 100%) with the ACS1 cloned from ghost chili pepper at the protein level.

A further embodiment is that the medium or long-chain carboxylic acid is 8-methyl-trans-6-nonenoic acid. Long chain carboxylic acids generally have 14 to 18 carbons, while medium-chain carboxylic acids generally have 8 to 13 carbons.

In one embodiment of the current invention, the feeding of medium to long-chain carboxylic acids to the cellular system comprises adding the medium long-chain carboxylic acid to the cellular system for use by the selected strains.

In an alternative embodiment, the feeding of medium to long-chain carboxylic acid to the cellular system comprises expressing the medium to long-chain carboxylic acid from a biosynthetic pathway in the cellular system.

In terms of product/commercial utility there are several dozen products containing capsaicin on the market in the United States and can be used in everything from analgesics to pest repellents as well as in foods and as a dietary supplements. Products containing capsaicin can be, for example, aerosols, liquids, or granular formulations.

As for the cellular system in the embodiment, it is selected from the group consisting of bacteria, yeast, and a combination thereof, or any cellular system that would allow the genetic transformation with the selected genes and thereafter the biosynthetic production of the desired capsaicinoids from the alternative feeding precursors. In a most preferred microbial system, *E. coli* are used to produce the desired capsaicinoid compounds.

An embodiment of the present disclosure is a biosynthetic method of making 8-methylnonenoyl-CoA comprising expressing an ACS in a cellular system, feeding 8-methyl-trans-6-nonenoic acid to the cellular system, growing the cellular system in a medium, and producing 8-methylnonenoyl-CoA. The ACS of the current invention, in some embodiments, is expressed from ACS1 cloned from ghost chili pepper. Alternatively, the ACS can be expressed from LCAS4 or LCAS5 cloned from *Arabidopsis*.

In another embodiment, the ACS of the invention is expressed from ACS2 cloned from *Capsicum* spp. Further, in some embodiments, the ACS is an ACS that shares a sequence identity of at least 66% (e.g., at least 70%, at least 80%, at least 90%, at least 95%, at least 99% or 100%) with the ACS1 cloned from ghost chili pepper. In another embodiment, the ACS is an ACS that shares a sequence similarity of at least 92% (e.g., 92%, 93%, 94%, 95%, 96%, 97%, 98%, 99% or 100%) at the protein level with the ACS1 cloned from ghost chili pepper.

In some aspects, the invention provides a biosynthetic method of making a capsaicinoid of interest comprising: expressing an ACS and CS in a transformed cellular system; growing the cellular system in a medium; and producing the capsaicinoid of interest.

In some embodiments, the ACS is cloned from a plant of the *Capsicum* genus. In some embodiments, the *Capsicum* genus plant is the ghost chili. In some embodiments, the ACS expressed is derived from a gene cloned from *Arabidopsis* based on LCAS4 or LCAS5. In some embodiments, the CS is cloned from a plant of the *Capsicum* genus. In some embodiments, the *Capsicum* genus plant is the ghost chili.

In some embodiments, the method further comprises feeding a source material to said cellular system in addition to culture media. In some embodiments, the source material is selected from the group consisting of: nonanoic acid; oil of pelargonium; octanoic acid; decanoic acid; vanillin; and, vanillyamine. In some embodiments, the source material is a mixture of two or more of the following: nonanoic; oil of pelargonium; octanoic acid; decanoic acid; vanillin; and, vanillyamine. In some embodiments, the source material is nonanoic acid. In some embodiments, said source material is selected from the group consisting of: C6 to C12 hydrocarbons that are medium to long chain fatty acids. In some embodiments, the source material is a mixture of two or more C6 to C12 hydrocarbons that are medium to long chain fatty acids.

In some embodiments, the transformed cellular system is selected from the group including yeast, non-capsaicinoid producing plants, algae and bacteria. In some embodiments, the cellular system is *E. coli*.

In some embodiments, the capsaicinoid of interest is capsaicin. In some embodiments, the capsaicinoid of interest is NV. In some embodiments, the capsaicinoid of interest is DHCP. In some embodiments, the capsaicinoids produced are a mixture comprising CP, NV and DHCP. In some embodiments, the capsaicinoid of interest is nordihydrocapsaicin.

In some embodiments, the ACS utilized is an ACS that shares a DNA sequence similarity of at least 75% (e.g., at least 75%, at least 80%, at least 85%, at least 90%, at least 95%, at least 99% or 100%) with SEQ ID NO: 3. In some embodiments, the ACS utilized is an ACS that shares a protein sequence similarity of at least 90% (e.g., at least 90%, at least 95%, at least 99% or 100%) with SEQ ID NO: 1. In some embodiments, the CS utilized is an CS that shares a DNA sequence similarity of at least 75% (e.g., at least 75%, at least 80%, at least 85%, at least 90%, at least 95%, at least 99% or 100%) with SEQ ID NO: 4. In some embodiments, the CS utilized is an CS that shares a protein sequence similarity of at least 90% (e.g., at least 90%, at least 95%, at least 99% or 100%) with SEQ ID NO: 2.

In some embodiments, the cellular system is selected from the group consisting of bacteria, yeast, plant cells, animal cells, an in vitro translation system and a combination thereof.

In some embodiments, producing the capsaicinoid of interest comprises: i) purifying crude product; and, ii) removing solvents under vacuum to provide a concentrated capsaicinoid product. In some embodiments, the crude product is purified by column chromatography. In some embodiments, the crude product is purified by acid-base extraction. In some embodiments, the crude product is purified by vacuum distillation. In some embodiments, said the product is purified by semi-preparative HPLC.

In some embodiments, the cellular system further comprises an aminotransferase which is capable of catalyzing the conversion of vanillin to vanillylamine.

In some embodiments, the transformed cellular system includes a CaUGT2 from *C. roseus*. In some embodiments, the transformed cellular system includes a CaUGT2 that shares a DNA sequence similarity of at least 75% (e.g., at least 75%, at least 80%, at least 85%, at least 90%, at least 95%, at least 99% or 100%) with SEQ ID NO: 5. In some embodiments, the transformed cellular system includes a CaUGT2 that shares a protein sequence similarity of at least 90% (e.g., at least 90%, at least 95%, at least 99% or 100%) with SEQ ID NO: 6.

In other aspects, the invention provides a capsaicinoid of interest produced by a transformed cellular system growing within a medium. In some embodiments, the transformed cellular system is selected from the group consisting of: yeast, non-capsaicinoid producing plants, algae and bacteria. In some embodiments, the transformed cellular system is transformed by the presence of an ACS and a CS derived from a plant of the *Capsicum* genus. In some embodiments, the ACS transformed into the cellular system is an ACS derived from *Arabidopsis* based on LCAS4 or LCAS5. In some embodiments, the transformed cellular system is transformed by the presence of an ACS and a CS derived from a plant of the *Capsicum* genus. In some embodiments, the transformed cellular system is transformed by the presence of an ACS and a CS derived the ghost chili.

In some embodiments, the method of producing further comprises feeding the transformed cellular system a specific source material. In some embodiments, the source material is selected from a group consisting of: nonanoic; oil of pelargonium; octanoic acid; decanoic acid; vanillin; and, vanillyamine. In some embodiments, the source material is selected from a mixture containing two or more of the following: nonanoic; oil of pelargonium; octanoic acid; decanoic acid; vanillin; and, vanillyamine.

In some embodiments, the capsaicinoid is CP. In some embodiments, said capsaicinoid is NV. In some embodiments, the capsaicinoid is DHCP. In some embodiments, the capsaicinoids produced are a mixture of CP, NV and DHCP. In some embodiments, the capsaicinoid is greater than 70% (e.g., greater than 70%, greater than 80%, greater than 90%, greater than 95%, greater than 98% or greater than 99%) pure. In some embodiments, the capsaicinoid content is greater than about 85% (e.g., greater than about 85%, greater than about 90%, greater than about 95%, greater than about 98%, or greater than about 99%) by weight on a dry basis. In some embodiments, the capsaicinoid is purified capsaicin.

In yet other aspects, the invention provides a method of producing a capsaicinoid of interest comprising feeding a transformed microbe culture a specific fatty acid precursor. In some embodiments, the capsaicinoid of interest is Capsaicin and the fatty acid precursor is 6E-8-methyl-6-nonenoic acid. In some embodiments, the capsaicinoid of interest is Dihydrocapsaicin and the fatty acid precursor is 8-Methyl nonanoic acid. In some embodiments, the capsaicinoid of interest is Nonivamide and the fatty acid precursor is nonanoic acid. In some embodiments, the capsaicinoid of interest is N-Vanilly octamide and the fatty acid precursor is octanoic acid. In some embodiments, the capsaicinoid of interest is N-vanilyl decanamide and the fatty acid precursor is decanoic acid. In some embodiments, the transformed culture is a microbe culture of yeast or bacteria.

In some embodiments, the microbe culture expresses an ACS that shares a DNA sequence similarity of at least 75% (e.g., at least 75%, at least 80%, at least 85%, at least 90%, at least 95%, at least 99% or 100%) with SEQ ID NO: 3. In some embodiments, the microbe culture expresses an ACS that shares a protein sequence similarity of at least 90% (e.g., at least 90%, at least 95%, at least 99% or 100%) with SEQ ID NO: 1. In some embodiments, the microbe culture expresses a CS that shares a DNA sequence similarity of at least 75% (e.g., at least 75%, at least 80%, at least 85%, at least 90%, at least 95%, at least 99% or 100%) with SEQ ID NO: 4. In some embodiments, the microbe culture expresses a CS that shares a protein sequence similarity of at least 90% (e.g., at least 90%, at least 95%, at least 99% or 100%) with SEQ ID NO: 2. In some embodiments, the microbe culture expresses a CaUGT2 that shares a DNA sequence similarity of at least 75% (e.g., at least 75%, at least 80%, at least 85%, at least 90%, at least 95%, at least 99% or 100%) with SEQ ID NO: 5. In some embodiments, the microbe culture expresses a CaUGT2 that shares a protein sequence similarity of at least 90% (e.g., at least 90%, at least 95%, at least 99% or 100%) with SEQ ID NO: 6.

In other aspects, the invention provides an analgesic composition for the topical treatment of pain in which the composition contains an effective amount of a capsaicinoid(s), wherein said analgesic composition is produced by any of the methods described herein wherein the improvement comprises producing said capsaicinoid in a microbial cellular system. In some embodiments, the effective amount is at least 0.0125 percent of a capsaicinoid of interest. In some embodiments, the capsaicinoid is selected from the group comprising: nonivamide, N-vanillylnonanamides, N-vanillylsulfonamides, N-vanillylureas, N-vanillylcarbamates, N[(substituted phenyl)methyl]alkylamides, methylene substituted N[(substituted phenyl)methyl]alkanamides, N[(substituted phenyl)methyl]-cis-monosaturated alkenamides, N[(substituted phenyl)methyl]diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamde, nonivamide, olvanil, N-oleyl-homovanillamidia, isovelleral, scalaradial, ancistrodial, and any combinations or mixtures thereof.

In other aspects, the invention provides a flavor and fragrance composition, wherein the flavor and fragrance composition has at least one capsaicinoid produced according to any of the methods described herein. In some embodiments, the capsaicinoid is selected from the group comprising: nonivamide, N-vanillylnonanamides, N-vanillylsulfonamides, N-vanillylureas, N-vanillylcarbamates, N[(substituted phenyl)methyl]alkylamides, methylene substituted N[(substituted phenyl)methyl]alkanamides, N[(substituted phenyl)methyl]-cis-monosaturated alkenamides, N[(substituted phenyl)methyl]diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamde, nonivamide, olvanil, N-oleyl-homovanillamidia, isovelleral, scalaradial, ancistrodial, and any combinations or mixtures thereof.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

Other features and advantages of this invention will become apparent in the following detailed description of preferred embodiments of this invention, taken with reference to the accompanying drawings.

BRIEF DESCRIPTION OF THE DRAWINGS

FIG. 3 is a reading of substrate and products, peak areas were measured at 280 nm.

DESCRIPTION OF THE PREFERRED EMBODIMENT

Figure 1:
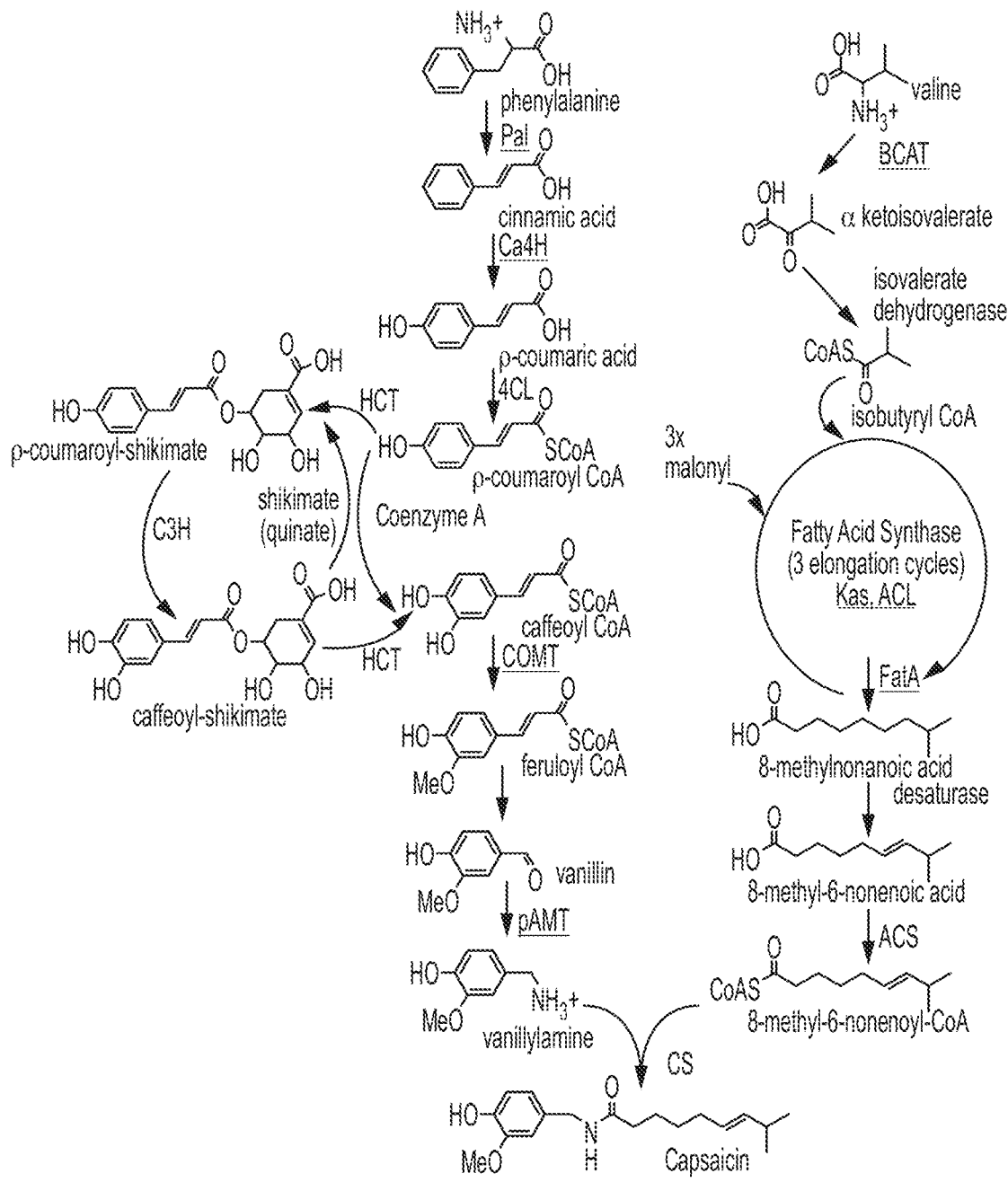
FIG. 1. shows the Capsaicinoid Biosynthetic Pathway. The aminotransferase (pAMT) catalyzes the formation of vanillyamine from vanillin.

The following abbreviations have designated meanings in the specification:
Explanation of Terms Used Herein:
  Capsaicin or CE is a colorless irritant phenolic amide $C_{18}H_{27}NO_3$ and is one of a series of phenolic amides found in various *Capsicum* species and hybrids thereof that gives hot peppers their hotness or pungency and that is used for food, medicine, and security applications. Pure CP is a volatile, hydrophobic, colorless, odorless, crystalline to waxy compound.

Capsaicinoid as used herein this refers to a class of irritant compounds, related to Capsaicin, that are responsible for the heat of chili peppers. They are irritants for mammals, including humans, and can produce a sensation of burning in any tissue with which they come into contact. The capsaicinoids are produced as secondary metabolites by chili peppers, probably as deterrents against certain mammals and fungi. Exemplary capsaicinoids include, but are not limited to: nonivamide, N-vanillylnonanamides, N-vanillylsulfonamides, N-vanillylureas, N-vanillylcarbamates, N[(substituted phenyl)methyl]alkylamides, methylene substituted N[(substituted phenyl)methyl]alkanamides, N[(substituted phenyl)methyl]-cis-monosaturated alkenamides, N[(substituted phenyl)methyl]diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamde, nonivamide, olvanil, N-oleyl-homovanillamidia, isovelleral, scalaradial, ancistrodial, and any combinations or mixtures thereof. Certain capsaicinoids are further described in Table 2.

Cellular system is any cells that provide for the expression of ectopic proteins. It includes bacteria, yeast, plant cells and animal cells. It includes both prokaryotic and eukaryotic cells. It also includes the in vitro expression of proteins based on cellular components, such as ribosomes.

Fatty Acids, C6-C12. According to the current invention a variety of fatty acids can be used as starting source materials. The source materials include vanillin, vanillylamine or their derivatives with modifications at the aromatic ring such as methylation, ethylation, or glycosylation; and more particularly 6-12 carbon straight chain or branched chain fatty acids or their derivatives such as hydroxy fatty acids (Ex: Hexanoic acid; Heptanoic acid; Octanoic acid; Nonanoic acid; Decanoic acid; Undecanoic acid; and, Dodecanoic acid) can be straight chain fatty acids or branched chain fatty acids and be used to make the capsaicinoids of the current invention.

Growing the Cellular System. Growing includes providing an appropriate medium that would allow cells to multiply and divide. It also includes providing resources so that cells or cellular components can translate and make recombinant proteins.

Protein Expression. Protein production can occur after gene expression. It consists of the stages after DNA has been transcribed to messenger RNA (mRNA). The mRNA is then translated into polypeptide chains, which are ultimately folded into proteins. DNA may be present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. Transduction is often used to describe virus-mediated DNA transfer. Transformation, transduction, and viral infection are included under the definition of transfection for this application.

Yeast. According to the current invention yeast as claimed herein are eukaryotic, single-celled microorganisms classified as members of the fungus kingdom. Yeast are unicellular organisms which evolved from multicellular ancestors but with some species useful for the current invention being those that have the ability to develop multicellular characteristics by forming strings of connected budding cells known as pseudohyphae or false hyphae.

Acronyms:
Pal, phenylalanine ammonia lyase;
Ca4H, cinnamic acid 4-hydroxylase;
4CL, 4-coumarate CoA ligase;
HCT, hydroxycinnamoyl transferase;
C3H, coumaroyl shikimate/quinate 3-hydroxylase;
COMT, caffeic acid O-methyltransferase; pAMT, aminotransferase;
BCAT, branched-chain amino acid transferase;
Kas, 3-keto-acyl ACP synthase;
ACL, acyl carrier protein;
FatA, acyl-ACP thioesterase;
ACS, acyl-CoA synthetase; and,
CS, capsaicin synthase.

DETAILED DESCRIPTION

The present invention relates, in some embodiments, to a system for an improved production method of CP, DHCP and NV as developed from specific feeding precursors.

Figure 2:
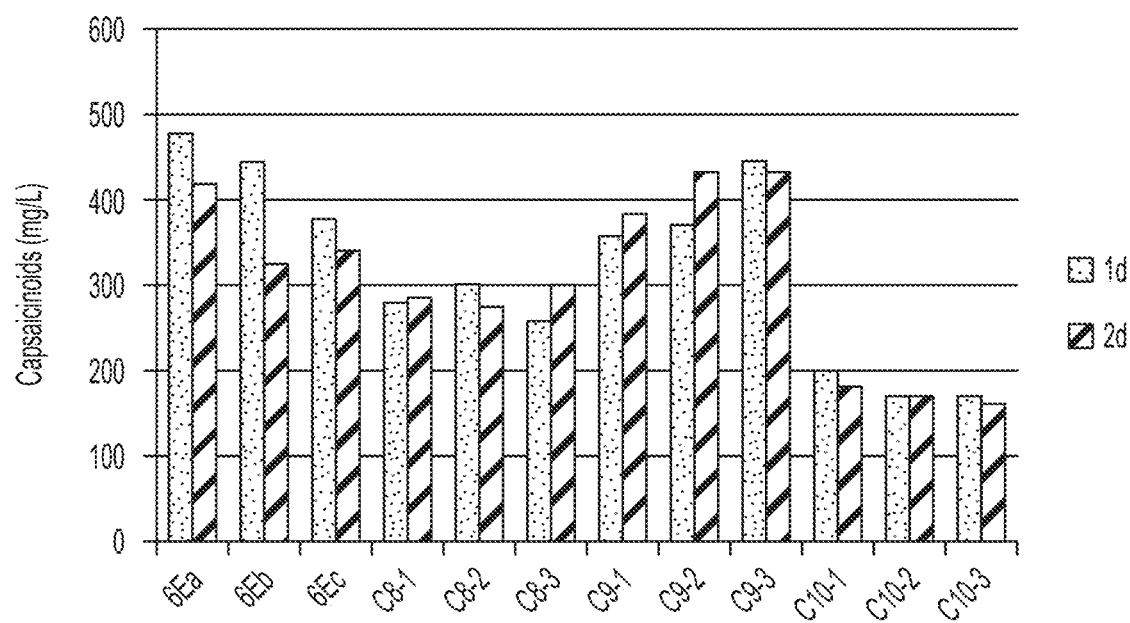
FIG. 2 shows the production levels of specific Capsaicinoid compounds according to an embodiment of the transformed cellular system of the invention. Production of CP (capsaicin), CP8 (N-vanilly octamide), CP9 (nonivamide) or CP10 (N-vanillyl decanamide) from 6E (6E-8-methyl nonenoic acid), C8:0 (octanoic acid or caprylic acid), C9:0 (nonanoic acid or pelargonic acid) and C10:0 (decanoic acid or capric acid), respectively. The experiment was performed in triplicate. Left bar in each pair is 1d. Right bar in each pair is 2d.

Nonivamide, also called pelargonic acid vanillylamide or PAVA (here "NV"), is one of trace capsaicinoids identified in hot peppers (FIG. 2; Constant et al., 1996). It is used as a food additive for pungent flavors. It is also used the pharmaceutical industry as an alternative to capsaicin. However, due to the extremely low content of nonivamide in hot peppers, using current plant extraction methods is not commercially viable so it has been exclusively made by chemical synthesis. Although chemically-synthesized nonivamide is readily available and cheap, non-natural compounds are not well perceived by consumers whose demand is in favor of natural products. To be natural, the chemicals have to be derived from the extraction of natural materials or to be transformed by enzymes or microbes from natural precursors, as provided in the methods of the current invention.

One aspect of the present invention are the DNA and corresponding protein sequences of the ACS and CS of the current invention. The DNA sequences for the ACS and CS enzymes were identified and removed from a ghost chili hybrid and inserted into plasmids for use in the current invention. Such sequences are provided herein as SEQ ID NO: 3 and SEQ ID NO: 4, respectively.

The present invention includes nucleic acid molecules and uses thereof in methods described herein, the nucleic acid molecules having nucleic acid sequences that hybridize to SEQ ID NO: 1 and SEQ ID NO: 2, respectively, or any complements thereof, or any cis elements thereof. The present invention also provides nucleic acid molecules and uses thereof in methods described herein, the nucleic acid molecules comprising a nucleic acid sequence selected from the group consisting of SEQ ID NO: 3 through SEQ ID NO: 4 for the ACS and CS sequences of the invention, any complements thereof, or any cis elements thereof, or any fragments thereof. (See Table 1, SEQ ID NOs: 3 and 4).

Additional embodiments include the use of ACS1 to modify the levels of capsaicinoids in pepper plants by overexpressing ACS1 utilizing standard known techniques for overexpression of genes in transformed plants. Another embodiment includes the use of ACS 1 to modulate the levels of capsaicinoids in pepper plants by knocking out or knocking down ACS1 utilizing standard known techniques for knocking out or knocking down expression of genes. Again, the overexpression or the knock out/knock down is by standard molecular cellular strategies and techniques known by a person of ordinary skill in the art. Another embodiment includes the use of ACS1 to generate acyl-CoAs and their downstream metabolites including fatty acids involving the expression or overexpression of ACS1. Another variation is the use of ACS1 to modulate the levels of acyl-CoAs and their downstream metabolites including fatty acids comprising knocking out or knocking down ACS1. Different specific capsaicinoids produced are determined by different fatty acids fed into the culture. (See Table 3).

The acyl CoAs that are made by the methods hereof could be utilized to make capsaicinoids of interest, and they would generally be of the medium chain variety. Again, although ACS1 can mediate the conversion of both medium chain- and long chain-carboxylic acids to acyl-CoAs, the medium chain activity is far more important than long chain activity as medium chain activity is the essential component in today's biofuel industry. The other importance as mentioned above for ACS1 is that it can be used to modify the capsaicinoid levels in plants through transgenic technology. However, ACS1 is not precluded from usage in regards to long chain acyl-CoAs. In an embodiment, a cellular system, such as a bacterial based system or a yeast based system can be modified to express ACS. The ACS could be ACS1 cloned from ghost pepper. Other ACSs suitable are one based on LCAS4 and LCAS5 from *Arabidopsis*. Other known ACS1 and ACS2 could also be expressed in the cellular systems. Appropriate substrate, such as 8-methyl-trans-6-nonenoic acid and 8-methylnonanoic acid, can then be fed to the cellular system. The substrates could also be expressed as part of a biosynthetic pathway within the cellular system. The cellular system is then incubated allowing for the biosynthetic production of 8-methyl-trans-6-nonenoyl-CoA or 8-methyl nonanoyl-CoA.

According to another embodiment of the current invention the efficiency of heterologous protein production in a microbial system can be enhanced by codon changes that alter the DNA sequences to one that may be preferred by the cellular system being used for expression but that varies from the original gene source organism without changing the eventual polypeptide produced. Approaches normally used to overcome this problem include targeted mutagenesis to remove rare codons or the addition of rare codon tRNAs in specific cell lines to move towards a codon sequence preferred by a host organism that will produce the polypeptide of interest. Recently, improvements in such "codon optimization" technology have enabled cost-effective production of synthetic genes, making this a feasible alternative and potentially useful for the current invention.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

Determination of Sequence Similarity Using Hybridization Techniques

Nucleic acid hybridization is a technique well known to those of skill in the art of DNA manipulation. The hybridization properties of a given pair of nucleic acids are an indication of their similarity or identity.

The term "hybridization" refers generally to the ability of nucleic acid molecules to join via complementary base strand pairing. Such hybridization may occur when nucleic acid molecules are contacted under appropriate conditions. "Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity," i.e., each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional low stringency and high stringency conditions are described herein and by Sambrook et al., MOLECULAR CLONING, A LABORATORY MANUAL, 2nd Ed., Cold Spring Harbor Press, Cold Spring Harbor, New York (1989) and by Haymes et al., NUCLEIC ACID HYBRIDIZATION, A PRACTICAL APPROACH, IRL Press, Washington, DC (1985). Departures from complete complementarity are permissible, as long as such departures do not completely preclude the capacity of the molecules to form a double-stranded structure.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL fish sperm DNA, and 0.1% (w/v) SDS, with an incubation at 55°

C. for several hours. Hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

A nucleic acid molecule preferably comprises a nucleic acid sequence that hybridizes, under low or high stringency conditions, with SEQ ID NO: 3 and SEQ ID NO: 4, any complements thereof, or any fragments thereof, or any cis elements thereof. A nucleic acid molecule most preferably comprises a nucleic acid sequence that hybridizes under high stringency conditions with SEQ ID NO: 3 and SEQ ID NO: 4, any complements thereof, or any fragments thereof, or any cis elements thereof.

Analysis of Sequence Similarity Using Identity Scoring

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, MA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity is preferably determined using the "Best Fit" or "Gap" program of the Sequence Analysis Software Package™ (Version 10; Genetics Computer Group, Inc., Madison, WI). "Gap" utilizes the algorithm of Needleman and Wunsch (Needleman and Wunsch, JOURNAL OF MOLECULAR BIOLOGY 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, ADVANCES IN APPLIED MATHEMATICS, 2:482-489, 1981, Smith et al., NUCLEIC ACIDS RESEARCH 11:2205-2220, 1983). The percent identity is most preferably determined using the "Best Fit" program.

Useful methods for determining sequence identity are also disclosed in the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; Altschul et al., J. MOL. BIOL. 215:403-410 (1990); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "substantial percent sequence identity" refers to a percent sequence identity of at least about 70% sequence identity, at least about 80% sequence identity, at least about 85% identity, at least about 90% sequence identity, or even greater sequence identity, such as about 98% or about 99% sequence identity. Thus, one embodiment of the invention is a polynucleotide molecule that has at least about 70% sequence identity, at least about 80% sequence identity, at least about 85% identity, at least about 90% sequence identity, or even greater sequence identity, such as about 98% or about 99% sequence identity with a polynucleotide sequence described herein. Polynucleotide molecules that have the activity of the ACS and CS genes of the current invention are capable of directing the production of a variety of capsaicinoids and have a substantial percent sequence identity to the polynucleotide sequences provided herein and are encompassed within the scope of this invention.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

In an alternative embodiment, the nucleic acid molecule comprises a nucleic acid sequence that exhibits 70% or greater identity, and more preferably at least 80 or greater, 85 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid molecule selected from the group consisting of SEQ ID NO: 3 and SEQ ID NO: 4, any complements thereof, any fragments thereof, or any cis elements thereof. The nucleic acid molecule preferably comprises a nucleic acid sequence that exhibits a 75% or greater sequence identity with a polynucleotide selected from the group consisting of SEQ ID NO: 3 and SEQ ID NO: 4, any complements thereof, any fragments thereof, or any cis elements thereof. The nucleic acid molecule more preferably comprises a nucleic acid sequence that exhibits an 80% or greater sequence identity with a polynucleotide selected from the group consisting of SEQ ID NO: 3 and SEQ ID NO: 4, any complements thereof, any fragments thereof, or any cis elements thereof. The nucleic acid molecule most preferably comprises a nucleic acid sequence that exhibits an 85% or greater sequence identity with a polynucleotide selected from the group consisting of SEQ ID NO: 3 and SEQ ID NO: 4, any complements thereof, any fragments thereof, or any cis elements thereof.

For purposes of this invention "percent identity" may also be determined using BLASTX version 2.0 for translated nucleotide sequences and BLASTN version 2.0 for polynucleotide sequences. In a preferred embodiment of the present invention, the presently disclosed corn genomic promoter sequences comprise nucleic acid molecules or fragments having a BLAST score of more than 200, preferably a BLAST score of more than 300, and even more preferably a BLAST score of more than 400 with their respective homologues.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Although the foregoing invention has been described in some detail by way of illustration and example for purposes of understanding, it will be apparent to those skilled in the art that certain changes and modifications may be practiced. Therefore, the description and examples should not be construed as limiting the scope of the invention, which is delineated by the appended claims.

Accordingly, it is to be understood that the embodiments of the invention herein providing for the production of specific capsaicinoids are merely illustrative of the application of the principles of the invention. It will be evident from the foregoing description that changes in the form, methods of use, and applications of the elements of the disclosed production methods and selected microbial strains may be resorted to without departing from the spirit of the invention, or the scope of the appended claims.

Example 1 mg/L of vanillylamine and 500 mg/L of individual fatty acid were fed into *E. coli*. culture overexpressing ghost chili ACS1 and CS genes. Production samples were taken one (1) day and two (2) days after the substrate feeding and analyzed by high-performance liquid chromatography (HPLC) (see FIG. 2).

As seen in FIGS. 1 and 2 nonivamide and other capsaicinoids were produced as a result of this experiment. NV is an amide of pelargonic acid (n-nonanoic acid) and vanillylamine. Nonivamide is widely used as a food additive for spicy flavors and a medicine for relieving arthritis and muscle pain.

The CP, DHCP and NV capsaicinoids produced herein were synthesized in modified *E. coli* cultures that were modified to carry the ACS and CS genes from ghost chili peppers. These genes allowed the properly fed selected strains to synthesize the capsaicinoids via the inserted acyltransferase CS that transfers the 8-methylnonenoyl moiety from 8-methylnonenoyl-CoA to vanillylamine to form an amide conjugate. Vanillylamine is formed from the phenylpropanoid pathway whereas the branched-chain fatty acid is derived from a branched-chain amino acid, e.g., valine (Curry, et al., 1999; Mazourek, et al., et al., 2009). The aminotransferase (pAMT) catalyzes the formation of vanillyamine from vanillin (FIG. 1). Glycerol stock of BL21 (DE3) culture co-overexpressing ACS1 and CS was used to inoculate 5 ml of TB (Terrific Broth) medium containing 100 mg/L of carbenicillin and 100 mg/L of spectinomycin and the culture was shaken at 37° C. overnight. Then the overnight culture was used to inoculate 20 ml of TB medium containing 100 mg/L of carbenicillin and 100 mg/L of spectinomycin. The culture was first grown at 37° C. to an OD600 of 0.4 and cooled down to 25° C. Then 1 mM IPTG was added to induce the expression of ACS1 and CS. After 3 h of incubation at 25° C., 500 mg/L of VN and 500 mg/L of each individual fatty acid were added to the culture and the culture was continued to be incubated at 25° C. Samples were taken at 24 h and 48 h after the feeding of substrates. Capsaicinoids were extracted from the culture by ethyl acetate and the ethyl acetate phase was analyzed by HPLC. The experiment was performed in triplicates.

In our previous application, we described a process for the production of CP and DHCP in *E. coli* cultures overexpressing ACS1 and CS genes from ghost chili pepper upon the feeding corresponding substrates (Table 1; Chen et al., 2015). According to the current invention we report the production of NV. According to the current invention the transformed cultures are fed specific fatty acids so that the product produced by such cultures is a single species of capsaicinoid (see Table 3). Of course this is an improvement in efficiency relative to plant based production where a mixture of various capsaicinoids with CP and DHCP are produced and extracted.

Although nonivamide has been identified as a naturally occurring capsaicinoid in *Capsicum* species (Constant et al. 1996), the content is so low that no natural nonivamide has been commercially used.

Inorganic or non-biological processes for the synthesis of capsaicin and analogues thereof have been reported, for example, by Crombie et al., (J. CHEM SOC., 1025-27 (1955)) describes an unambiguous synthesis of capsaicin, N-(4-hydroxy-3-methoxybenzyl)-8-methylnon-trans-6-enamide, the active principle in red pepper. Other organic pathways have been shown in U.S. Pat. No. 4,493,848 issued to LaHann et al., and U.S. Pat. No. 5,094,782 issued to Chen et al.

Capsaicinoids, have long been used as an experimental tool because of their selective action on the small diameter afferent nerve fibers C-fibers and A-delta fibers that are believed to signal pain. From studies in animals, capsaicinoids appears to trigger C-fiber membrane depolarization by opening cation channels permeable to calcium and sodium. Recently one of the receptors for capsaicinoid effects has been cloned.

In most chili peppers, vanillylamine is formed from phenylalanine via ferulic acid, vanillin and related compounds, and capsaicinoid is produced from vanillyamine and branched chain fatty acid by capsaicin synthase (FIG. 1).

Synthetic Biology

Genetically engineered microbes have become an increasingly important platform for the production of drugs, chemicals, and biofuels from renewable resources (Du et al., 2011). These biotechnological products, when used in food, can be labeled 'natural' in food sector according to current regulations (Häusler and Münch, 1997).

Exemplary capsaicinoids include, but are not limited to: nonivamide, N-vanillylnonanamides, N-vanillylsulfonamides, N-vanillylureas, N-vanillylcarbamates, N[(substituted phenyl)methyl]alkylamides, methylene substituted N[(substituted phenyl)methyl]alkanamides, N[(substituted phenyl)methyl]-cis-monosaturated alkenamides, N[(substituted phenyl)methyl]diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamde, nonivamide, olvanil, N-oleyl-homovanillamidia, isovelleral, scalaradial, ancistrodial, and any combinations or mixtures thereof.

Previously, an *E. coli* fermentation platform was developed where various capsaicinoids could be produced upon the feeding of fatty acids and vanillylamine/vanillin (Chen et al. 2015). As described herein, the production of nonivamide by this system is also possible (FIG. 2).

Producing Acyl-CoAs: Cloning

Applicants amplified ACS1 gene from the cDNA of the green fruits of the ghost chili pepper using the primers of ACS1-sumo-F: CGC GAA CAG ATT GGA GGT GCAA-CAGATAAATITATTATTG and ACS1-sumo-R: GTG GCG GCC GCT CTA TTA TCACTTGGTACCCTTGTACAT. The resulting PCR product was purified on 1% agarose gel and mixed with linear pETite N-His SUMO Kan expression vector (Lucigen, Middleton, Wis.). The DNA mixture was used to transform HI-control 10G chemically competent cells by heat shock (Lucigen). The gene insertion was fully sequenced and the encoded amino acid sequence was aligned with that of ACS1. As shown previously (Chen et al., 2015), these two sequences are new due to a replacement mutation in which Ile476 in the known *Capsicum* sequence is replaced by a valine residue in ghost pepper ACS1 (SEQ ID NO: 1 provided herein). The sequence of ghost pepper ACS1 was used to blast the *Arabidopsis* database (http://www.arabidopsis.org) and identified LCAS4 and LCAS5 as homologues. As previously shown, these three sequences share a sequence identity of 66% and a sequence similarity of 92%. Both LCAS4 and LCAS5 have been biochemically characterized as long chain acyl-CoA synthetases that participate in fatty acid and glycerolipid metabolism (Shockey et al., 2003). Recently, LCAS4 is demonstrated to be required for the formation of pollen coat lipids in *Arabidopsis* (Belza and Jessen, 2005).

Expression

Applicants used pETite N-His SUMO-ghost pepper ACS1 to transform HI-Control BL21(DE3) cells (Lucigen) and the expression of His-SUMO-ACS1 was induced by 0.5 mM IPTG at 16° C. for 20 hrs. The fusion protein was purified by Ni-NTA column. ACS 1 has a molecular weight of ca. 73.5 Kd and the size of His-SUMO tag is ca. 12 Kd. The His-SUMO-ghost pepper ACS1 fusion protein on SDS-PAGE migrated close to the predicted size.

Products

Applicants used an HPLC-based method to measure the activity of ghost pepper ACS1 (Chen et al., 2011). Briefly, reaction mixtures (400 µE) contained 0.1 M Tris-HCl, pH 7.5, 2 mM DTI, 5 mM ATP, 10 mM MgCl2, 0.5 mM CoA, 0.1% Triton and 200 µM carboxylic acids. The reaction was initiated by adding 20 µL of purified enzyme and stopped after 30 minutes by addition of 20 micromolar acetic acid. HPLC was performed with Dionex-UltiMate© 3000 LC Systems (Thermo Scientific) using an Acclaim® 120 CI 8 reversed-phase column (Thermo Scientific; 3µ, 120 A, 150χ3 mm). The mobile phase consisted of solvent A (0.1% trifluoroacetic acid) and solvent B (acetonitrile). The gradient elution procedure was as follows: 0 to 5 min, 5% of B; 5 to 9 min, a linear gradient from 5 to 80% of B; 9 to 11 min, 80% of B; 11 to 12 min, 5% of B. The flow rate was 0.6 ml/min. The diode array detector collected data in the 200- to 400-nm range. For detection and quantification of substrate and products, peak areas were measured at 257 nm.

Figure 8:
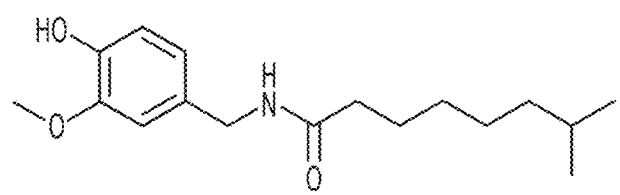
FIG. 8 shows the structure of nordihydrocapsaicin (7M-CP). Nordihydrocapsaicin (7M-CP) is the third most abundant CP in hot peppers, which occupies ca. 7% of total capsaicinoids.

As shown in FIG. 8, ACS1 had activities in various medium against long chain carboxylic acids with the highest activity against capric acid (CIO). In contrast, ACS1 did not show any activity against acetic acid (C2) or butyric acid (C4)—short chain carboxylic acid.

Applicants then used 8-methyl-trans-6-nonenoic acid (6E), the endogenous intermediate in the capsaicinoid biosynthetic pathway or its reduced product, 8-methylnonanoic acid (8M), as a substrate to assay ACS1 activity. As shown in FIG. 2, ACS1 showed activities with both substrates with a higher activity for 6E. Applicants collected the corresponding HPLC fractions for the product peaks and dried them over a SpeedVac Concentrator for further MS/MS identification.

Confirmation of Product

Methanol:Water:Acetonitrile buffer. 10 µE was used for direct infusion using the TriVersa Nanomate® (Advion, Ithaca, N.Y.). The mass spectrometer, LTQ-Orbitrap Velos (Thermo Fisher Scientific, Waltham, Mass.), was operated in negative ionization mode. The MS survey scan was performed in the FT cell from a mass range of 300 to 2,000 m/z. The resolution was set to 60,000@400 m/z. CID fragmentation was used for MS/MS, and detection was done in the ion trap with an isolation window of 1.5 m/z Fragmentation was performed with normalized collision energies of 35%. As shown previously the MS data matched the molecular weight of 8-methyl-trans-6-nonenoyl-CoA and 8-methyl nonanoyl-CoA, respectively.

The pH optimal of ACS1 against 8-methylnonanoic acid was also studied. Acetate, phosphate, Tris and glycine/NaOH buffers were used to provide a pH range from 4.0 to 10.5. The optical pH of ACS1 is ca. 9.5. Accordingly, applicants have identified a novel medium/long chain acyl-CoA synthetase in ghost hot pepper which provides the substrate for capsaicin synthase. In addition, the novel enzyme may also have applications in biofuel industry for making medium-chain fatty acid derivatives.

Production of Nordihydrocapsaicin with Addition of CaUGT2 from *C. roseus*

According to the current invention a variety of selected capsaicinoids can be produced through the use of selected starting materials. The current invention also provides for the production of specific capsaicinoid compounds through the use of specific enzymes. This process allows applicants to produce specific and desirable capsaicinoids in quantities not previously possible so that the medicinal, food and fragrances uses can be fully determined and modifications can be made to assist in solubilization and dosing.

According to the current invention, glycosylation of capsaicin and 8-nordihydrocapsaicin by cultured cells of *Catharanthus roseus* has been reported (Shimoda et al. 2007). However, the gene that is responsible for this specific activity has not been previously identified. Other workers (Kaminaga et al. (2004)) identified two genes encoding UDP-glucosyltransferases, CaUGT1 and CaUGT2 from *C. roseus* and demonstrated that they catalyzed the formation of curcumin monoglucoside from curcumin and also conversion of curcumin monoglucoside to curcumin diglucoside without mention of capsaicinoid activity. In fact, these authors also tested the activity of CaUGT2 against capsaicin but found it could not glycosylate capsaicin (Kaminage et al., 2004). However, according to the current invention we demonstrated that CaUGT2 can catalyze the formation of capsaicins glucoside both in vitro and in vivo.

Figure 6:
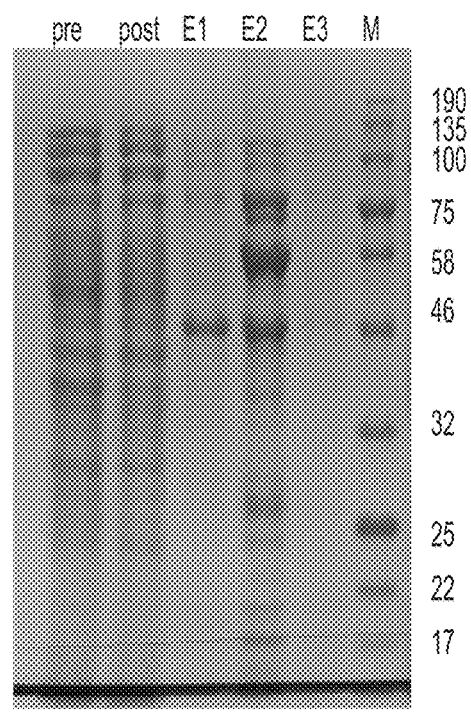
FIG. 6 shows Ni-NTA affinity chromatography of CaUGT2. Pre, pre-column; post, post-column; E1, E2, E3, fractions collected from column. His-tagged CaUGT2 has a molecular weight ca. 58 kD.
Figure 7:
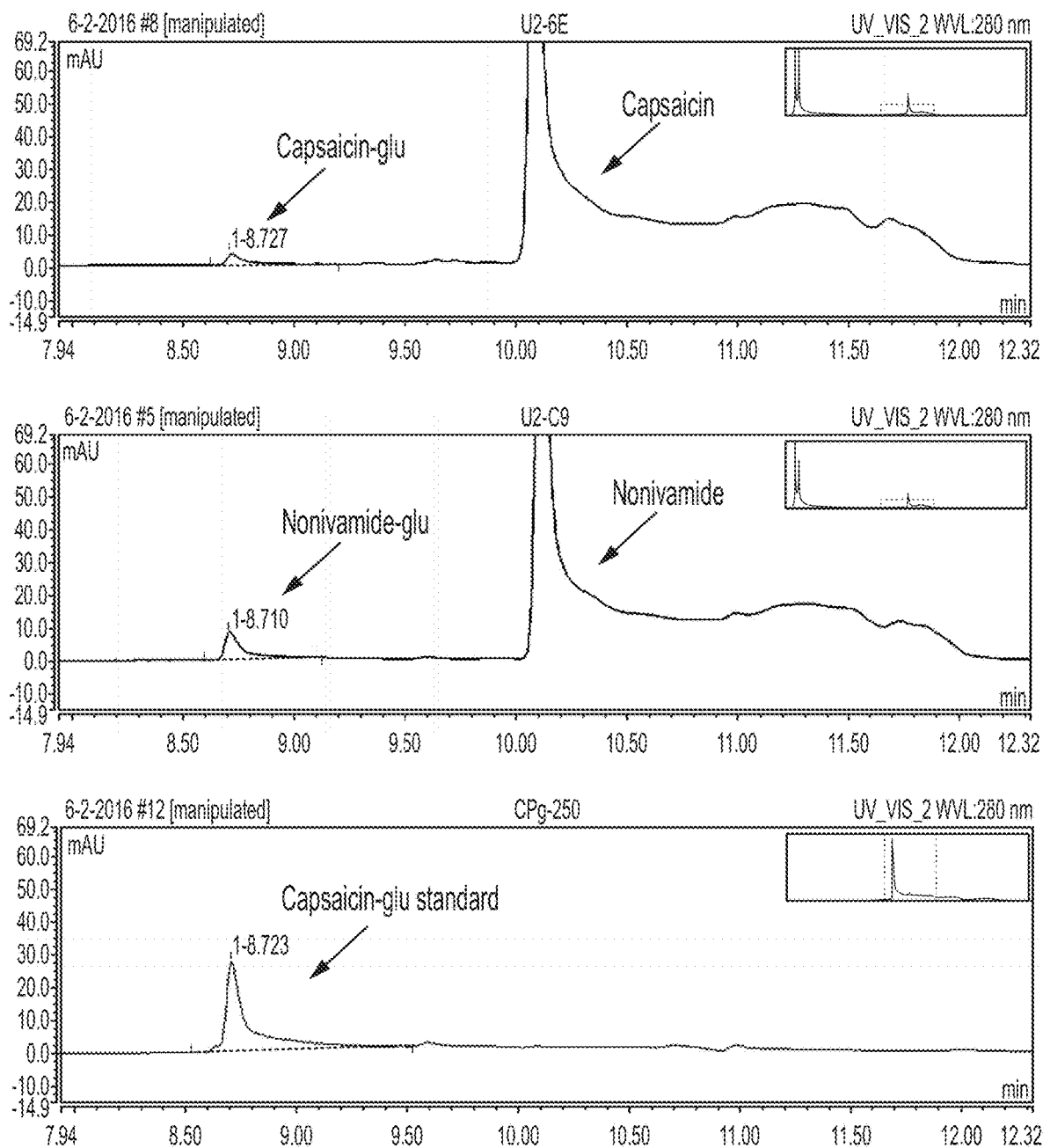
FIG. 7 shows production of capsaicin-glu and nonivamide-glu by CaUGT2 in vitro.

According to the current invention the *Catharanthus roseus* CaUGT2 gene (GenBank: AB159213.1) was synthesized and codon-optimized for *E. coli* and cloned into a pDEST17 vector (see Table 5). The resulting pDEST17-CaUGT2 plasmid was used to transform BL21 Star (DE3) competent cells. The transformed culture was first grown at 37° C. in LB(AMP+) medium until OD600=0.4 and then cool down to 16° C. and 1 mM IPTG was added to induce the expression of CaUGT2 protein. Cells were harvested 16 h after induction by centrifugation and soluble protein was extracted by B-PER™ Bacterial Protein Extraction Reagent (Thermo Fisher Scientific) according to the manufacture's instruction and further purified by Ni-NTA affinity chromatography (FIG. 6). It was determined that the use of this modified enzyme could produce capsaicinoids of interest (FIGS. 7-10).

Figure 9:
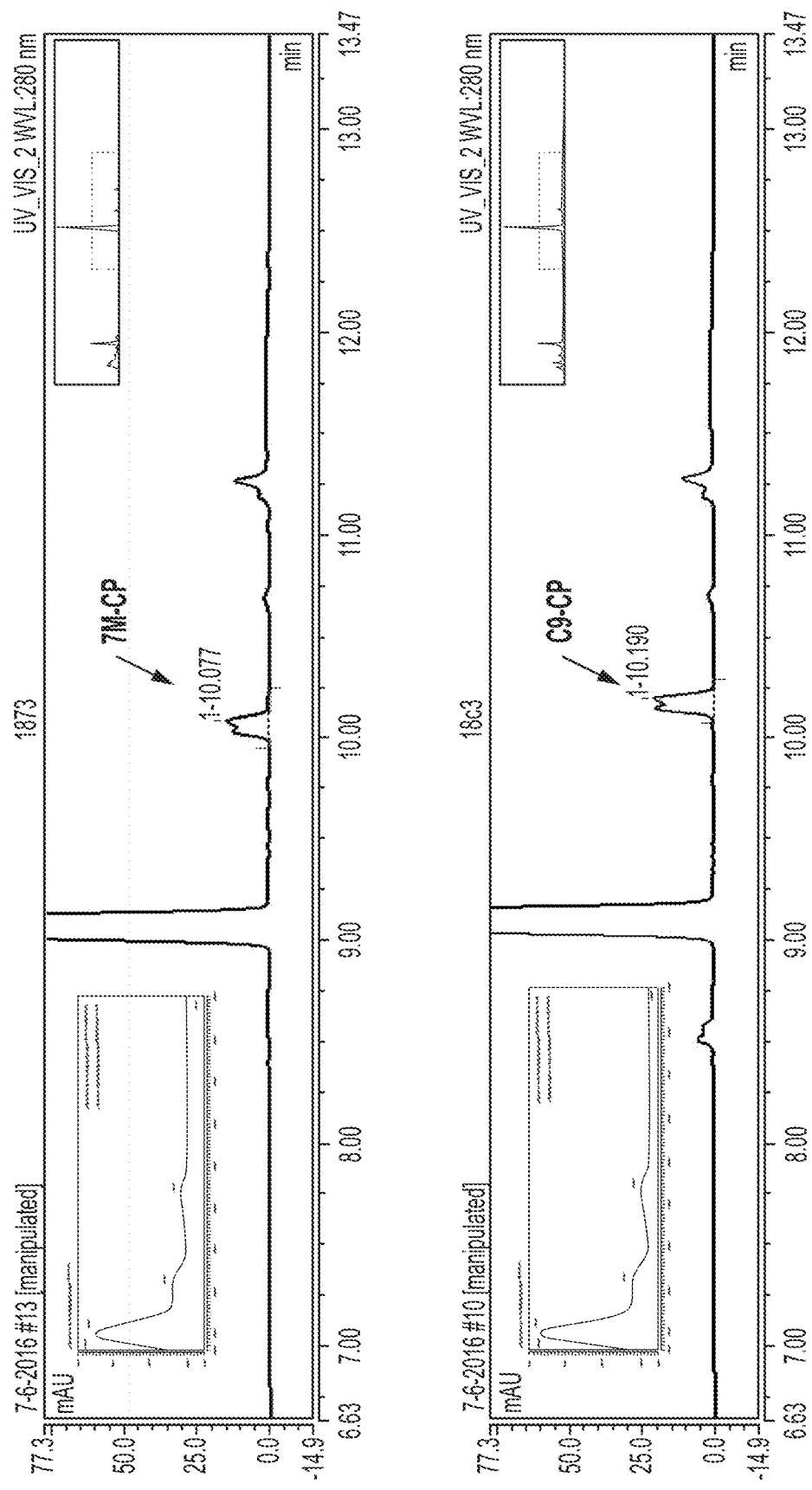
FIG. 9 shows HPLC profiles of 7M-CP and C9-CP production.
Figure 10:
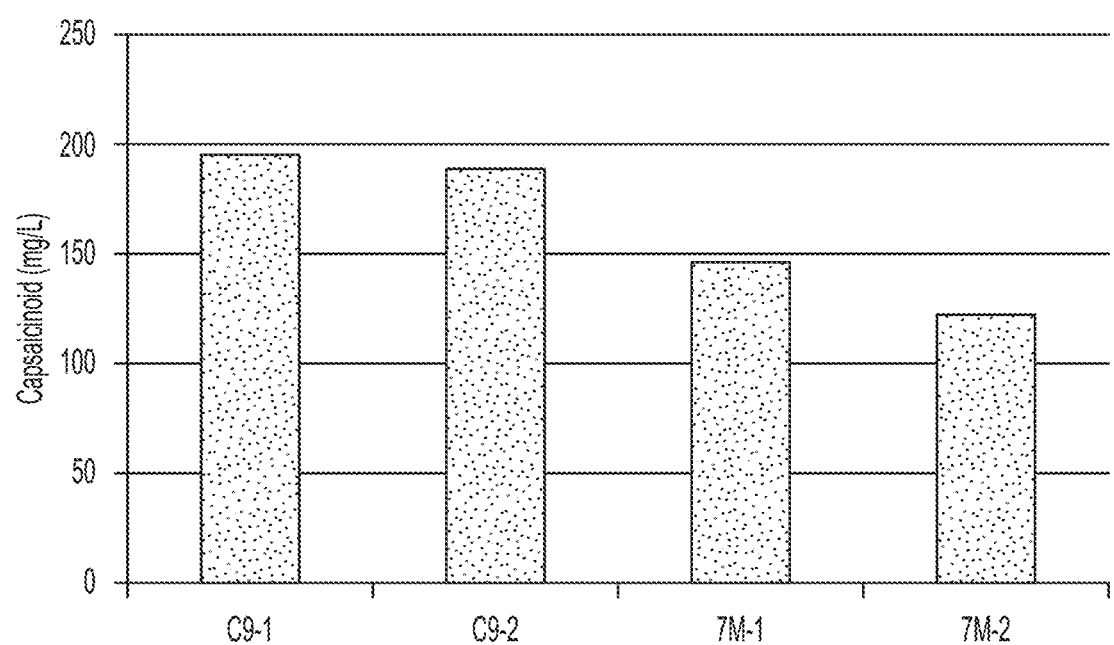
FIG. 10 shows a comparison of C9-CP and 7M-CP production in the same culture system. The experiment was performed in duplicate.

In addition, in vivo biotransformation of capsaicin and nonivamide was performed for the production of capsaicin-glu and nonivamide-glu, respectively using BL21 Star (DE3) culture overexpressing CaUGT2 with a titer of ca. 5 mg/L. Further, the fatty acid chain of 7M-CP is derived from the fatty acid, 7-methyloctanoic acid (7M) or isopelargonic acid. When 7M was fed into this culture system, 7M-CP was produced (FIGS. 9 and 10). As shown in FIG. 9, the retention time of 7M-CP (10.077 min) is slightly different from that of C9-CP (10.190 min) and their UV spectra are almost identical (see inserted picture in FIG. 9). The levels of 7M-CP and C9-CP in the cultures were also quantified (FIG. 10). The titer of 7M-CP was slightly lower than that of C9-CP.

Production of Capsaicinoids

Figure 3:
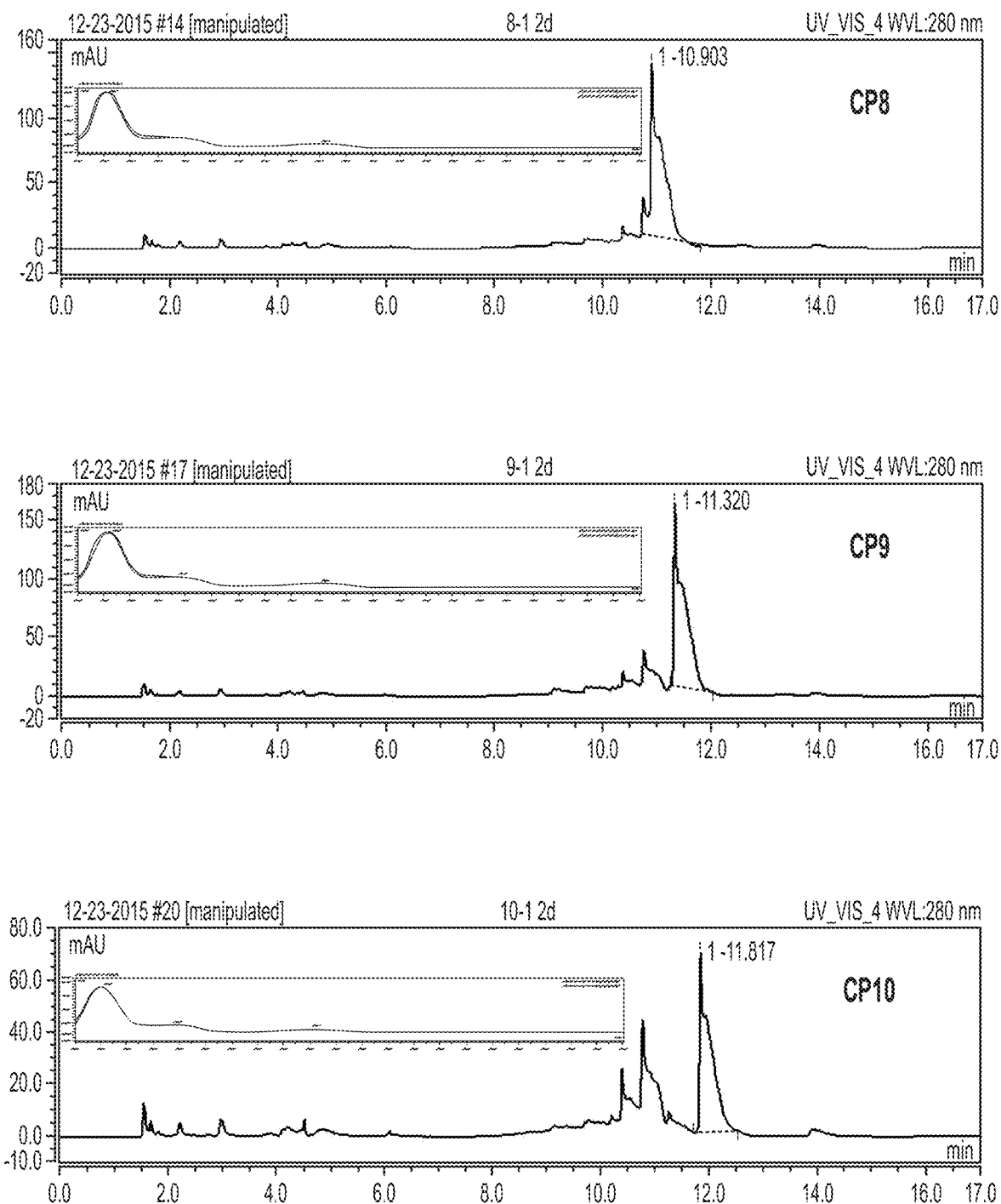
FIG. 3 shows HPLC Profiles of the preferred Cellular System, in particular HPLC profiles of crude ethyl acetate extracts from E. coli cultures fed with C8:0, C9:0 and C10:0, respectively. CP8 (N-vanilly octamide), CP9 (nonivamide) and CP10 (N-vanillyl decanamide) had retention times of 10.9, 11.3 and 11.8 min, respectively. The inserted pictures are their UV-Vis spectra.
Figure 4:
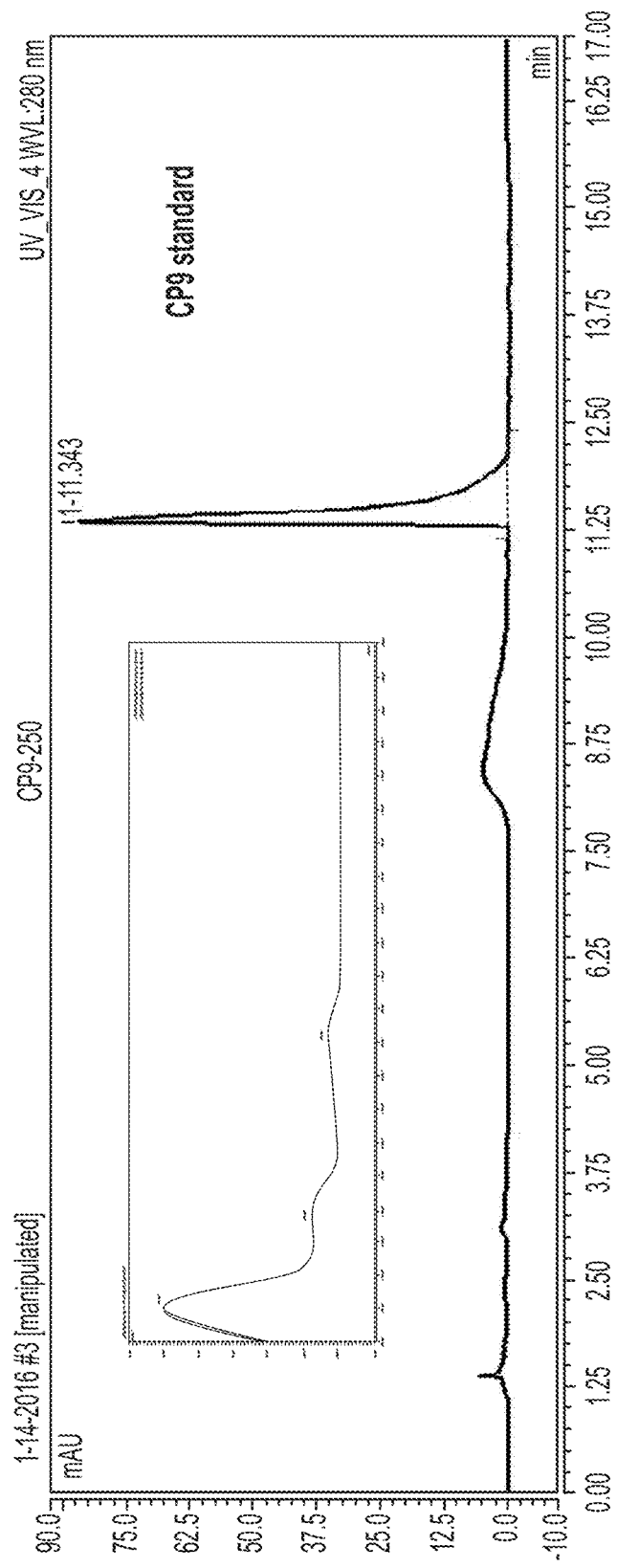
FIG. 4 shows a HPLC profile of the Nonivamide standard to compare with an embodiment of the cellular system of the invention.
Figure 5:
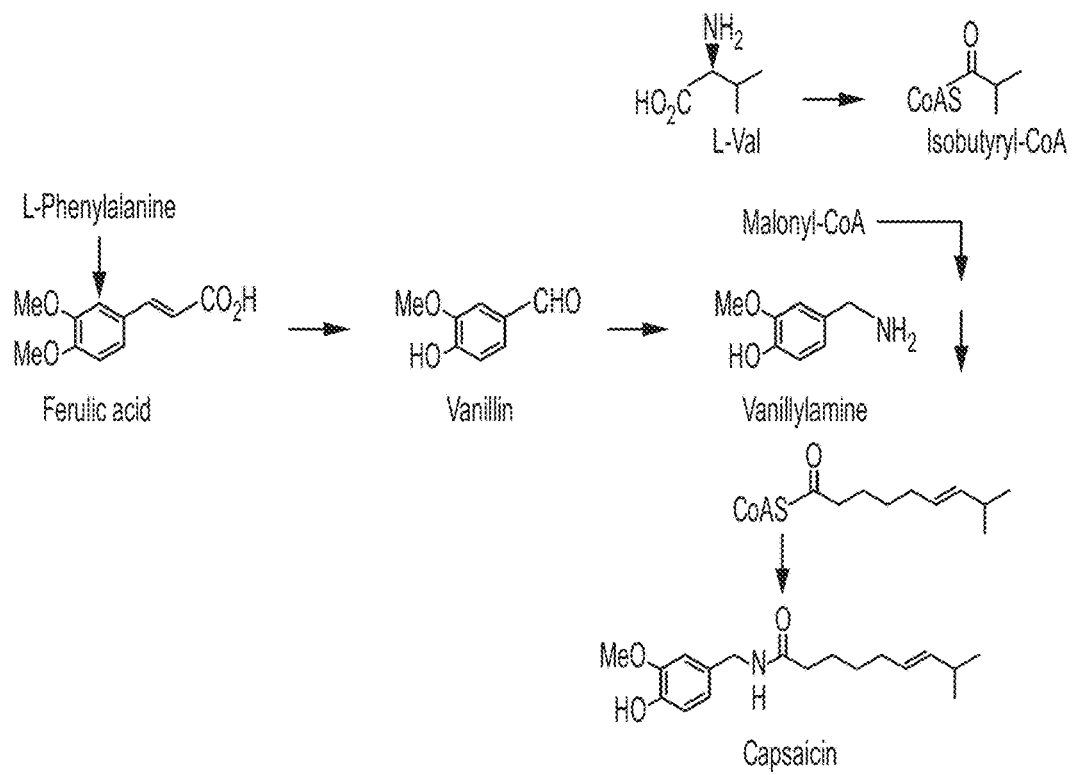
FIG. 5 shows production of Capsaicin from vanillin with the presence of the pAMT synthase.

As shown in FIG. 2, our culture system had a CP9 titer similar to that of CP although the titers for CP 8 and CP10 were slightly lower. On HPLC, CP8 (N-vanilly octamide), CP9 (nonivamide) or CP10 (N-vanillyl decanamide) had retention times of 10.9, 11.3 and 11.8 min, respectively. However, their UV spectra are very similar to each other (FIG. 3). The retention time and UV spectrum of CP9 match those of nonivamide standard very well (FIG. 4).

HPLC was performed with Dionex-UltiMate® 3000 LC Systems (Thermo Scientific) using an Acclaim® 120 C18 reversed-phase column (Thermo Scientific; 3µ, 120 Å, 150×3 mm). The mobile phase consisted of solvent A (0.1% trifluoroacetic acid) and solvent B (acetonitrile). The gradient elution procedure was as follows: 0 to 5 min, 5% of B; 5 to 9 min, a linear gradient from 5 to 80% of B; 9 to 11 min, 80% of B; 11 to 12 min, 5% of B. The flow rate was 0.6 ml/min. The diode array detector collected data in the 200- to 400-nm range. For detection and quantification of substrate and products, peak areas were measured at 280 nm (FIGS. 3 and 4).

Statement of Industrial Applicability/Technical Field

This disclosure has applicability in the food, medicinal, and pharmacological industries. This disclosure relates generally to a method for the biosynthetic production of capsaicinoids via a modified microbial strain.

Tables Referenced in the Specification

TABLE 1

Amino acid sequences of ACS1 and CS cloned from ghost chili pepper.

| | |
|---|---|
| ACS1 | MATDKFIIEVESAKPAKDGRPSMGPVYRSIFAKHGFPPPIPGLD SCWDIFRMSVEKYPNNRMLGRREIVDGKPGKYVWMSYKEVYDIV IKVGNSIRSIGVDVGDKCGIYGANCPEWIISMEACNAHGLYCVP LYDTLGAGAVEFIISHAEVTIAFVEEKKLPELLKTFPNASKYLK TIVSFGKVTPEQKKELEEFGVVLYSWDEFLQLGSGKQFDLPVKK KEDICTIMYTSGTTGDPKGVLISNTSIVTLIAGVRRFLGSVDES LNVDDVYLSYLPLAHIFDRVIEECFIHHGASIGFWRGDVKLLTE DIGELKPTVFCAVPRVLDRIYSGLQQKIAAGGFLKSTLFNLAYA YKHHNLKKGRKHFEASPLSDKVVFSKVKEGLGGRVRLILSGAAP LAAHVEAFLRVVACCHVLQGYGLTETCAGTFVSLPNRYDMLGTV GPPVPNVDVCLESVPEMSYDALSSTPRGEVCVRGDVLFSGYYKR EDLTKEVMIDGWFHTGDVGEWQPNGSLKIIDRKKNIFKLSQGEY VAVENLENIYGNNPIIDSIWIYGNSFESFLVAVINPNQRAVEQW AEVNGLSGDFASLCEKPEVKEYILRELTKTGKEKKLKGFEFLKA VHLDPVPFDMERDLLTPTFKKKRPQLLKYYKDVIDSMYKGTK |
| CS | MAFALPSSLVSVCDKSFIKPSSLTPSKLRFHKLSFIDQSLSNMY IPCAFFYPKVQQRLEDSKNSDELSHIAHLLQTSLSQTLVSYYPY AGKLKDNATVDCNDMGAEFLSVRIKCSMSEILDHPHASLAESIV LPKDLPWANNCEGGNLLVVQVSKFDCGGIAISVCFSHKIGDGCS LLNFLNDWSSVTRDHTTTALVPSPRFVGDSVFSTKKYGSLITPQ ILSDLNECVQKRLIFPTDKLDALRAKVAEESGVKNPTRAEVVSA LLFKCATKASSSMLPSKLVHFLNIRTMIKPRLPRNAIGNLSSIF SIEATNMQDMELPTLVRNLRKEVEVAYKKDQVEQNELILEVVES MREGKLPFENMDGYENVYTCSNLCKYPYYTVDFGWGRPERVCLG NGPSKNAFFLKDYKAGQGVEARVMLHKQQMSEFERNEELLEFIA |

In the above protein sequences ACS shall be considered SEQ ID NO 1 and CS shall be considered SEQ ID NO 2.

TABLE 1

Nucleic Acid sequences of ACS1 and CS cloned from ghost chili pepper.

| | |
|---|---|
| ACS1 | ATGGCTACGGACAAATTTATTATTGAAGTTGAATCAGCAAAACCG GCAAAAGATGGTCGCCCGAGCATGGGCCCGGTCTATCGTTCGATC TTTGCGAAACATGGCTTTCCGCCGCCGATCCCGGGTCTGGATTCA TGCTGGGACATTTTTCGTATGTCGGTGGAAAAATATCCGAACAAT CGCATGCTGGGCCGTCGCGAAATTGTTGATGGCAAACCGGGTAAA TACGTTTGGATGAGCTACAAAGAAGTCTACGACATCGTTATCAAA GTCGGTAACAGTATTCGTTCCATCGGCGTGGATGTTGGTGACAAA TGCGGCATTTATGGTGCAAACTGTCCGGAATGGATTATCAGCATG GAAGCATGCAATGCTCATGGCCTGTATTGTGTCCCGCTGTACGAT ACCCTGGGCGCAGGTGCTGTGGAATTTATTATCTCTCACGCGGAA GTGACCATCGCCTTCGTTGAAGAGAAAAAACTGCCGGAACTGCTG AAAACCTTTCCGAATGCGAGCAAATATCTGAAAACCATTGTCTCT TTCGGCAAAGTGACGCCGGAACAGAAGAAAGAACTGGAAGAATTT GGTGTGGTTCTGTACAGTTGGGATGAATTTCTGCAGCTGGGCTCC GGTAAACAATTCGATCTGCCGGTGAAAAAGAAAGAAGATATTTGC ACCATCATGTATACGAGCGGCACCACGGGTGATCCGAAAGGTGTG CTGATTTCAAACACCTCGATTGTGACGCTGATCGCCGGTGTTCGT CGCTTTCTGGGCTCAGTTGATGAATCGCTGAATGTGGATGACGTT TATCTGTCATACCTGCCGCTGGCACATATTTTTGACCGTGTGATC GAAGAATGCTTCATTCATCACGGCGCTTCGATCGGTTTTTGGCGC GGCGATGTGAAACTGCTGACCGAAGACATTGGCGAACTGAAACCG ACGGTTTTCTGTGCGGTCCCGCGTGTGCTGGATCGCATCTATTCA GGTCTGCAGCAAAAAATTGCGGCCGGCGGTTTTCTGAAATCGACC CTGTTCAACCTGGCGTATGCCTACAAACATCACAATCTGAAGAAA GGCCGCAAACACTTTGAAGCCAGCCCGCTGTCTGATAAAGTCGTG TTCAGTAAAGTGAAAGAAGGCCTGGGCGGTCGTGTTCGCCTGATT CTGTCCGGTGCGGCTCCGCTGGCCGGCACATGTGGAAGCGTTTCTG CGTGTTGTCGCCTGCTGTCACGTTCTGCAGGGCTATGGTCTGACC GAAACGTGCGCAGGCACCTTCGTGAGTCTGCCGAACCGCTACGAT ATGCTGGGCACGGTTGGTCCGCCGGTCCCGAATGTCGATGTGTGC CTGGAAACGTGCCGGAAATGTCTTATGACGCTCTGAGCTCTACC CCGCGTGGTGAAGTTTGTGTCCGCGGCGATGTTCTGTTTTCCGGT TATTACAAACGTGAAGACCTGACCAAAGAAGTTATGATTGATGGC TGGTTCCATACGGGCGACGTCGGTGAATGGCAGCCGAACGGTAGC CTGAAAATCATCGATCGTAAGAAAAACATCTTCAAACTGTCTCAA GGCGAATATGTGGCCGTTGAAAACCTGGAAAATATTTACGGCAAC |

TABLE 1-continued

Nucleic Acid sequences of ACS1 and
CS cloned from ghost chili pepper.

AATCCGATTATCGACAGCATTTGGATCTATGGTAACAGTTTTGAA
TCCTTCCTGGTCGCGGTGATCAACCCGAATCAGCGTGCAGTCGAA
CAATGGGCTGAAGTGAATGGCCTGAGTGGTGATTTCGCCTCCCTG
TGTGAAAAACCGGAAGTGAAAGAATACATTCTGCGCGAACTGACC
AAAACGGGCAAAGAGAAAAAACTGAAAGGTTTCGAATTTCTGAAA
GCAGTTCATCTGGACCCGGTGCCGTTTGATATGGAACGTGACCTG
CTGACCCCGACGTTCAAGAAAAACGTCCGCAACTGCTGAAATAC
TATAAAGATGTGATCGACTCAATGTATAAAGGCACGAAATAA

CS  ATGGCGTTCGCACTGCCGTCGAGTCTGGTCTCTGTGTGTGATAAA
TCCTTCATCAAGCCGAGTTCGCTGACCCCGAGCAAACTGCGTTTT
CATAAACTGAGCTTCATTGATCAGTCTCTGAGTAATATGTATATC
CCGTGCGCCTTTTTCTACCCGAAAGTGCAGCAACGTCTGGAAGAT
TCTAAGAACAGTGACGAACTGTCTCATATTGCACACCTGCTGCAG
ACGTCCCTGTCACAAACGCTGGTTAGCTATTACCCGTATGCTGGC
AAACTGAAGGATAACGCGACCGTGGATTGCAATGACATGGGTGCC
GAATTTCTGAGCGTTCGCATTAAATGTTCGATGAGCGAAATCCTG
GATCATCCGCACGCGTCGCTGGCCGAAAGCATTGTGCTGCCGAAA
GACCTGCCGTGGGCTAACAATTGCGAAGGCGGTAACCTGCTGGTT
GTGCAGGTCTCGAAGTTTGATTGCGGCGGTATTGCGATCTCTGTG
TGTTTCAGTCATAAAATCGGCGACGGTTGTAGCCTGCTGAACTTT

TABLE 1-continued

Nucleic Acid sequences of ACS1 and
CS cloned from ghost chili pepper.

CTGAATGATTGGAGCTCTGTCACCCGTGACCACACCACGACCGCC
CTGGTGCCGTCTCCGCGTTTTGTCGGTGATTCCGTGTTCTCAACC
AAAAAGTATGGTTCCCTGATTACGCCGCAAATCCTGTCAGACCTG
AATGAATGCGTGCAAAAACGTCTGATCTTCCCGACCGATAAACTG
GACGCACTGCGCGCTAAGGTGGCGGAAGAATCGGGCGTTAAAAAC
CCGACCCGTGCTGAAGTCGTGAGCGCGCTGCTGTTTAAATGTGCC
ACGAAGGCAAGTTCCTCAATGCTGCCGTCCAAGCTGGTTCATTTC
CTGAATATTCGCACCATGATCAAACCGCGTCTGCCGCGCAACGCC
ATTGGTAATCTGTCGAGCATTTTTAGCATCGAAGCAACCAATATG
CAGGATATGGAACTGCCGACGCTGGTTCGTAACCTGCGCAAAGAA
GTGGAAGTTGCGTACAAAAAGGATCAGGTCGAACAAAACGAACTG
ATCCTGGAAGTTGTCGAATCCATGCGTGAAGGCAAACTGCCGTTT
GAAAACATGGATGGTTATGAAAATGTGTACACCTGCTCAAACCTG
TGTAAATATCCGTATTACACGGTTGACTTCGGCTGGGGTCGTCCG
GAACGCGTCTGTCTGGGCAACGGTCCGTCTAAGAACGCGTTTTTC
CTGAAGGATTACAAGGCCGGCCAGGGTGTTGAAGCACGTGTCATG
CTGCACAAACAGCAAATGAGTGAATTTGAACGCAACGAAGAACTG
CTGGAATTTATTGCATAA

In the above nucleic acid sequences ACS shall be considered SEQ ID NO: 3 and CS shall be considered SEQ ID NO: 4.

TABLE 2

| Capsaicinoid Name | Abbrev. | Typical relative amount | Scoville heat units | Chemical structure |
|---|---|---|---|---|
| Capsaicin | C | 69% | 16,000,000 | 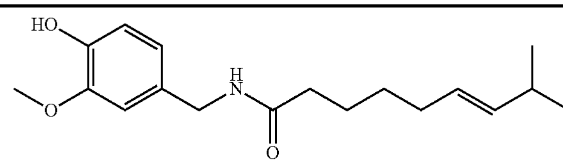 |
| Dihydrocapsaicin | DHCP | 22% | 15,000,000 | 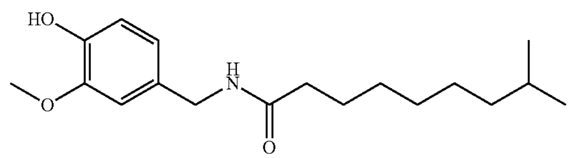 [SMILES: COc1cc(CNC(=O)CCCCCCC(C)C)ccc1O] |
| Nordihydrocapsaicin | NDHC | 7% | 9,100,000 | 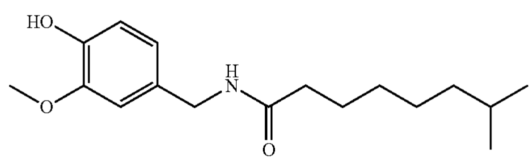 [SMILES: COc1cc(CNC(=O)CCCCCC(C)C)ccc1O] |
| Homodihydrocapsaicin | HDHC | 1% | 8,600,000 | 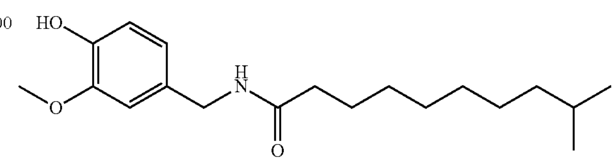 |
| Homocapsaicin | HC | 1% | 8,600,000 | 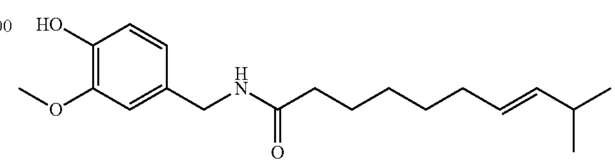 |
| Nonivamide | NV | | 9,200,000 | 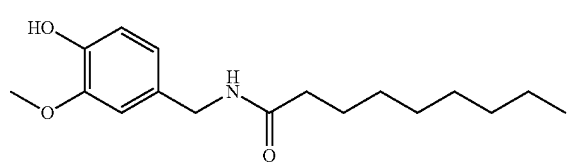 [SMILES: CCCCCCCCC(=O)NCc1ccc(O)c(OC)c1] |

TABLE 3

Feeding Schedule for the Production of Specific Capsaicinoids

| Fatty Acid Fed Into the Microbial Culture | Specific Capsaicinoid Produced |
| --- | --- |
| 6E-8-methyl-6-nonenoic acid | Capsaicin (CP) |
| 8-Methyl nonanoic acid | Dihydrocapsaicin (DHCP) |
| Pelargonic Acid (nonanoic acid) | Nonivamide (NV) |
| Capyrlic Acid (octanoic acid) | N-Vanilly octamide |
| Capric Acid (decanoic acid) | N-vanilyl decanamide |

TABLE 4

$^{13}$C Isotope Analysis of Capsaicinoid Samples

| Sample | $\delta^{13}C$ ‰ |
| --- | --- |
| CP | −30.1 |
| DHCP | −28.0 |
| NV | −28.8 |
| NV standard | −30.2 |
| Natural CP | −31.5 |
| In Planta capsacinoid* mixture | −31.9 |

*taken from a Chinese fern used in experimentation

TABLE 5

Sequence of codon-optimized CaUGT2

| CaUGT2 DNA | ATGGTTAATCAATTACACATCTTCAATTTCCCGTTTATGGCGC<br>AGGGTCACATGTTACCGGCGTTGGATATGGCGAATCTGTTCAC<br>TTCAAGAGGCGTAAAAGTTACACTGATTACCACTCATCAACAC<br>GTGCCAATGTTTACGAAGAGCATCGAACGCTCGCGTAATTCTG<br>GTTTCGATATCTCAATCCAAAGCATTAAATTCCCGGCGAGCGA<br>AGTAGGCTTACCTGAAGGTATCGAATCATTGGATCAGGTTAGC<br>GGCGATGACGAAATGCTGCCGAAATTCATGCGCGGTGTTAACC<br>TGTTACAACAGCCATTAGAACAATTGCTGCAAGAATCACGTCC<br>GCATTGTTTATTGAGCGATATGTTTTTCCCTTGGACAACGGAA<br>AGTGCTGCAAAATTCGGCATTCCGCGCCTGTTATTTCACGGTT<br>CTTGCTCATTCGCTCGTCGGCCGCGGAATCTGTGCGTAGAAA<br>TAAGCCTTTTGAAAACGTCTCCACCGATACTGAAGAATTTGTT<br>GTGCCAGACTTGCCGCATCAAATTAAACTGACAAGAACGCAGA<br>TCAGTACCTATGAACGCGAAAACATCGAATCCGATTTCACTAA<br>GATGCTGAAGAAAGTTCGTGACAGCGAAAGTACATCCTACGGT<br>GTCGTAGTTAATTCTTTCTACGAATTAGAACCAGATTACGCAG<br>ACTATTACATTAACGTTTTGGGCCGTAAAGCCTGGCATATCGG<br>TCCGTTTTTGCTGTGTAACAAACTGCAAGCAGAAGATAAGGCC<br>CAGAGAGGTAAAAAGTCAGCAATTGATGCCGACGAATGTCTGA<br>ATTGGTTAGACAGTAAACAACCTAACTCCGTGATCTATTTGTG<br>CTTTGGCTCGATGGCGAATCTGAACTCTGCTCAATTGCACGAA<br>ATTGCTACTGCACTGGAATCTTCAGGCCAGAATTTCATCTGGG<br>TGGTCAGAAAATGCGTCGATGAAGAAAACAGCAGTAAGTGGTT<br>TCCTGAAGGTTTCGAAGAACGCACCAAAGAAAAGGGCCTGATT<br>ATCAAAGGTTGGGCACCACAGACTTTAATTTTGGAACATGAAT<br>CGGTGGGCGCCTTTGTCACACACTGTGGTTGGAACTCTACGTT<br>GGAAGGCATCTGCGCGGGTGTACCTCTGGTTACATGGCCATTT<br>TTCGCTGAACAATTTTTCAACGAAAAACTGATCACCGAAGTAT<br>TAAAGACTGGTTACGGCGTTGGTGCCCGTCAGTGGAGTAGAGT<br>GTCCACGGAAATTATCAAAGGCGAAGCCATTGCGAATGCTATC<br>AACCGCGTGATGGTCGGCGATGAAGCAGTCGAAATGAGAAATC<br>GCGCCAAAGACCTGAAAGAAAAGGCGCGTAAGGCTTTAGAAGA<br>AGATGGCTCCTCGTATAGAGACTTGACCGCGCTGATTGAAGAA<br>CTGGGTGCTTACCGCTCTCAGGTGGAACGTAAACAACAGGATT<br>AA |
| CaUGT2 Amino acid | MVNQLHIFNFPFMAQGHMLPALDMANLFTSRGVKVTLITTHQH<br>VPMFTKSIERSRNSGFDISIQSIKFPASEVGLPEGIESLDQVS<br>GDDEMLPKFMRGVNLLQQPLEQLLQESRPHCLLSDMFFPWTTE<br>SAAKFGIPRLLFHGSCSFALSAAESVRRNKPFENVSTDTEEFV<br>VPDLPHQIKLTRTQISTYERENIESDFTKMLKKVRDSESTSYG<br>VVVNSFYELEPDYADYYINVLGRKAWHIGPFLLCNKLQAEDKA<br>QRGKKSAIDADECLNWLDSKQPNSVIYLCFGSMANLNSAQLHE<br>IATALESSGQNFIWVVRKCVDEENSSKWFPEGFEERTKEKGLI<br>IKGWAPQTLILEHESVGAFVTHCGWNSTLEGICAGVPLVTWPF<br>FAEQFFNEKLITEVLKTGYGVGARQWSRVSTEIIKGEAIANAI<br>NRVMVGDEAVEMRNRAKDLKEKARKALEEDGSSYRDLTALIEE<br>LGAYRSQVERKQQD |

LITERATURE CITED AND INCORPORATED BY REFERENCE

1. Aza-Gonzalez C. et al., (2011), *Molecular biology of capsaicinoid biosynthesis in chili pepper (Capsicum spp.)*. PLANT CELL REP. 30: 695-706.
2. Belza A, Jessen A B. (2005), *Bioactive food stimulants of sympathetic activity: effect on 24-h energy expenditure and fat oxidation*. EUR J CLIN NUTR., 59:733-41.
3. Bosland and Baral, (2007), *'Bhut Jolokia'—The world's hottest known chile pepper is a putative naturally occurring interspecific hybrid*, HORTSCIENCE 42:222-24.
4. Batchelor and Jones, (2000), *Determination of the Scoville Heat Value for Hot Sauces and Chilies: An HPLC Experiment*, J. CHEM. EDUC., 77 (2), p 266.
5. Catchpole et al., (2003), *Extraction of chili, black pepper, and ginger with near critical CO2, propane, and dimethyl ether: analysis of the extracts by quantitative nuclear magnetic resonance*, J. AGRICULTURAL AND FOOD CHEMISTRY 51: 4853-60.
6. Caterina M J., et al., (1997), *The capsaicin receptor: a heat-activated ion channel in the pain pathway*, NATURE 389, 816-24.
7. Constant H L et al., (1996), *Nonivamide, a constituent of Capsicum oleoresin*, JOURNAL OF NATURAL PRODUCTS, 59: 425-26.
8. Crombie et al., (1955). *Amides of vegetable origin. Part VI. Synthesis of capsaicin*, J. CHEM SOC., 1025-27.
9. Curry, J. et al., (1999), *Transcripts for possible capsaicinoid biosynthetic genes are different accumulated in pungent and non-pungent Capsicum spp.*, PLANT SCI. 148: 47-57.
10. Du J et al., (2011), *Engineering microbial factories for synthesis of value-added products*, J IND MICROBIOL BIOTECHNOL. 38: 873-90.
11. Garces-Claver A. et al., (2007). *Identification, validation and survey of a single nucleotide polymorphism (SNP) associated with pungency in Capsicum spp.* THEOR APPL GENET 115: 907-16.
12. Govindarajan and Sathyanarayana (1991), *Capsicum-production, technology, chemistry, and quality. Part V. Impact on physiology, pharmacology, nutrition, and metabolism; structure, pungency, pain, and desensitization sequences*, CRITICAL REVIEWS IN FOOD SCIENCE AND NUTRITION 29(6):435-74.
13. Häusler A, and Münch T., (1997), *Microbial production of natural flavors*, ASM NEWS 63:551-59.
14. Higashiguchi F., et al., (2006) *Purification and structure determination of glucosides of capsaicin and dihydrocapsaicin from various Capsicum fruits*, J AGRIC FOOD CHEM. 54: 5948-5953.
15. Jordt S E. and Julius D., (2002), *Molecular basis for species-specific sensitivity to "hot" chili peppers*. CELL. 108: 421-30.
16. Kaminaga Y. et al., (2004) *Molecular cloning and characterization of a glucosyltransferase catalyzing glucosylation of curcumin in cultured Catharanthus roseus cells*. FEBS LETT. 567: 197-202.

17. Kometani, T. et al., (1993) *Glucosylation of capsaicin by cell suspension cultures of Coffea arabica.* BIOSCI. BIOTECHNOL. BIOCHEM. 57, 2192-2193.
18. Mazourek, et al., (2009). *A Dynamic Interface for Capsaicinoid Systems Biology*, PLANT PHYS., 150:1806-21.
19. Prasad B C., (2006), *Characterization of capsaicin synthase and identification of its gene (csy1) for pungency factor capsaicin in pepper (Capsicum sp.).* PROC NATL. ACAD SCI USA. 103: 13315-20.
20. Prasad B C. et al., (2008), *Characterization of capsaicin synthase and identification of its gene (csy1) for pungency factor capsaicin in pepper (Capsicum sp.).* PROC NATL. ACAD SCI USA. 105: 20558.
21. Reilly C A. et al., (2001), *Determination of capsaicin, dihydrocapsaicin, and nonivamide in self-defense weapons by liquid chromatography-mass spectrometry and liquid chromatography-tandem mass spectrometry.* J. CHROMATOGR A. 912: 259-67.
22. Stewart C. et al., (2005) *The Pun1 gene for pungency in pepper encodes a putative acyltransferase*, PLANT J. 42: 675-88.
23. Stewart C. et al., (2007) *Genetic control of pungency in C. chinense via the Pun1 locus.* J EXP BOT. 58: 979-91.
24. Shimoda K., et al., (2007) *Glycosylation of capsaicin and 8-nordihydrocapsaicin by cultured cells of Catharanthus roseus.* PHYTOCHEMISTRY 68: 1391-96.
25. Shockey J M. Et al., (2003), *Arabidopsis contains a large superfamily of acyl-activating enzymes: phylogenetic and biochemical analysis reveals a new class of acyl-coenzyme A synthetases.* PLANT PHYSIOL 132 1065-76.
26. Suzuki T. et al., (1980) *Intracellular localization of capsaicin and its analogs capsaicinoid in Capsicum fruit, microscopic investigation of the structure of the placenta of Capsicum annuum var annuum cv. Karayatsubusa.* PLANT CELL PHYSIOL 21 839-53.
27. Suzuki T and Iwai K, (1984), *Constituents of red pepper spices: chemistry, biochemistry, pharmacology* and *food science of the pungent principle of Capsicum species*. In A Brossi, ed, THE ALKALOIDS: CHEMISTRY AND PHARMACOLOGY, Vol 23. Academic Press, Orlando, Fla., pp 227-99.
28. Thomas B V. Et al., (1998), *Simple method for quantitation of capsaicinoids in peppers using capillary gas chromatography.* J AGRIC FOOD CHEM., 46:2655-63.
29. Tominaga M. and Tominaga T., (2005), *Structure and function of TRPV1*, PFLUGERS ARCH. EUR J PHYSIOL.; 451: 143-50.
30. Walsh and Hoot, (2001), *Phylogenetic relationships of Capsicum (Solanaceae) using DNA sequences from two noncoding regions: The chloroplast atpB-rbcL spacer region and nuclear waxy introns*, INT. J. PLANT SCI. 162: 1409-18.
31. Weber N. et al., (2014), *Biocatalytic potential of vanillin aminotransferase from Capsicum chinense.* BMC BIOTECHNOL. 14:25.
32. Yao et al., (1994), *Supercritical carbon dioxide extraction of Scotch Bonnet (Capsicum annuum) and quantification of capsaicin and dihydrocapsaicin*, J. AGR. FOOD CHEM. 42:1303-05.

PATENTS CITED AND INCORPORATED BY REFERENCE

1. Chen H. et al., (2015) Methods of using capsaicin synthase for the microbial production of capsaicinoids. PCT/US2015/011729.
2. Chen et al., U.S. Pat. No. 5,094,782.
3. LaHann et al., U.S. Pat. No. 4,493,848.
4. Zhou R., and Yu X., (2014) Methods of making vanillin via the microbial fermentation of ferulic acid from eugenol using a plant dehydrogenase. PCT/US2014/063952.

```
SEQUENCE LISTING

Sequence total quantity: 6
SEQ ID NO: 1            moltype = AA  length = 658
FEATURE                 Location/Qualifiers
source                  1..658
                        mol_type = protein
                        note = Bhut Jolokia
                        organism = unidentified
SEQUENCE: 1
MATDKFIIEV ESAKPAKDGR PSMGPVYRSI FAKHGFPPPI PGLDSCWDIF RMSVEKYPNN  60
RMLGRREIVD GKPGKYVWMS YKEVYDIVIK VGNSIRSIGV DVGDKCGIYG ANCPEWIISM  120
EACNAHGLYC VPLYDTLGAG AVEFIISHAE VTIAFVEEKK LPELLKTFPN ASKYLKTIVS  180
FGKVTPEQKK ELEEFGVVLY SWDEFLQLGS GKQFDLPVKK KEDICTIMYT SGTTGDPKGV  240
LISNTSIVTL IAGVRRFLGS VDESLNVDDV YLSYLPLAHI FDRVIEECFI HHGASIGFWR  300
GDVKLLTEDI GELKPTVFCA VPRVLDRIYS GLQQKIAAGG FLKSTLFNLA YAYKHHNLKK  360
GRKHFEASPL SDKVVFSKVK EGLGGRVRLI LSGAAPLAAH VEAFLRVVAC CHVLQGYGLT  420
ETCAGTFVSL PNRYDMLGTV GPPVPNVDVC LESVPEMSYD ALSSTPRGEV CVRGDVLFSG  480
YYKREDLTKE VMIDGWFHTG DVGEWQPNGS LKIIDRKKNI FKLSQGEYVA VENLENIYGN  540
NPIIDSIWIY GNSFESFLVA VINPNQRAVE QWAEVNGLSG DFASLCEKPE VKEYILRELT  600
KTGKEKKLKG FEFLKAVHLD PVPFDMERDL LTPTFKKKRP QLLKYYKDVI DSMYKGTK    658

SEQ ID NO: 2            moltype = AA  length = 440
FEATURE                 Location/Qualifiers
source                  1..440
                        mol_type = protein
                        note = Bhut Jolokia
                        organism = unidentified
SEQUENCE: 2
MAFALPSSLV SVCDKSFIKP SSLTPSKLRF HKLSFIDQSL SNMYIPCAFF YPKVQQRLED  60
SKNSDELSHI AHLLQTSLSQ TLVSYYPYAG KLKDNATVDC NDMGAEFLSV RIKCSMSEIL  120
DHPHASLAES IVLPKDLPWA NNCEGGNLLV VQVSKFDCGG IAISVCFSHK IGDGCSLLNF  180
LNDWSSVTRD HTTTALVPSP RFVGDSVFST KKYGSLITPQ ILSDLNECVQ KRLIFPTDKL  240
DALRAKVAEE SGVKNPTRAE VVSALLFKCA TKASSSMLPS KLVHFLNIRT MIKPRLPRNA  300
IGNLSSIFSI EATNMQDMEL PTLVRNLRKE VEVAYKKDQV EQNELILEVV ESMREGKLPF  360
```

```
ENMDGYENVY TCSNLCKYPY YTVDFGWGRP ERVCLGNGPS KNAFFLKDYK AGQGVEARVM    420
LHKQQMSEFE RNEELLEFIA                                                440

SEQ ID NO: 3            moltype = DNA   length = 1977
FEATURE                 Location/Qualifiers
source                  1..1977
                        mol_type = genomic DNA
                        note = Bhut Jolokia
                        organism = unidentified
SEQUENCE: 3
atggctacgg acaaatttat tattgaagtt gaatcagcaa aaccggcaaa agatggtcgc     60
ccgagcatgg gcccggtcta tcgttcgatc tttgcgaaac atggctttcc gccgccgatc    120
ccgggtctgg attcatgctg ggacattttt cgtatgtcgg tggaaaaata tccgaacaat    180
cgcatgctgg gccgtcgcga aattgttgat ggcaaacggg gtaaatacgt ttggatgagc    240
tacaaagaag tctacgacat cgttatcaaa gtcggtaaca gtattcgttc catcggcgtg    300
gatgttggtg acaaatgcgg catttatggt gcaaactgtc cggaatggat tatcagcatg    360
gaagcatgca atgctcatgg cctgtattgt gtcccgctgt acgataccct gggcgcaggt    420
gctgtggaat ttattatctc tcacgcggaa gtgaccatcg ccttcgttga agagaaaaaa    480
ctgccggaac tgctgaaaac cttttccgaat gcgagcaaat atctgaaaac cattgtctct    540
ttcggcaaag tgacgccgga acagaagaaa gaactggaag aatttggtgt ggttctgtac    600
agttgggatg aatttctgca gctgggctcc ggtaaacaat tcgatctgcc ggtgaaaaag    660
aaagaagata tttgcaccat catgtatacg agcggcacca cgggtgatcc gaaaggtgtg    720
ctgatttcaa acacctcgat tgtgacgctg atcgccggtg ttcgtcgctt tctgggctca    780
gttgatgaat cgctgaatgt ggatgacgtt tatctgtcat acctgccgct ggcacatatt    840
tttgaccgtg tgatcgaaga atgcttcatt catcacggcg cttcgatcgg tttttggcgc    900
ggcgatgtga aactgctgac cgaagacatt ggcgaactga aaccgacggt tttctgtgca    960
gtcccgcgtg tgctggatcg catctattca ggtctgcagc aaaaaattgc ggccggcggt   1020
tttctgaaat cgaccctgtt caacctggcg tatgcctaca acatcacaa tctgaagaaa   1080
ggccgcaaac actttgaagc cagcccgctg tctgataaag tcgtgttcag taaagtgaaa   1140
gaaggcctgg gcgtcgtgt tcgcctgatt ctgtccgatg cggctccgct ggccgcacat   1200
gtggaagcgt ttctgtgt gtgcgcctgc tgtcacgttc tgcagggcta tggtctgacc   1260
gaaacgtgcg caggcacctt cgtgagtctg ccgaaccgct acgatatgct gggcacggtt   1320
ggtccgccgg tcccgaatgt cgatgtgtgc ctggaaagcg tgccggaaat gtcttatgac   1380
gctctgagct ctaccccgcg tggtgaagtt tgtgtccgcg gcgatgttct gttttccggt   1440
tattacaaac gtgaagacct gaccaaagaa gttatgattg atggctggtt ccatacggtg   1500
gacgtcggtg aatggcagcc gaacggtagc ctgaaaatca tcgatcgtaa gaaaaacatc   1560
ttcaaactgt ctcaaggcga atatgtgccg ttgaaaaacc tggaaaatat ttacggcaac   1620
aatccgatta tcgacagcat ttggatctat ggtaacagtt tgaatccttt cctggtcgcg   1680
gtgatcaacc cgaatcagcg tgcagtcgaa caatgggcta aagtaatgg cctgagtggt   1740
gatttcgcct ccctgtgtga aaaaccggaa gtgaaagaat acattctgcg cgaactgacc   1800
aaaacgggca agagaaaaa actgaaaggt tcgaatttc tgaaagcagt tcatctggac   1860
ccggtgccgt tgatatgga acgtgacctg ctgaccccga cgttcaagaa aaaacgtccg   1920
caactgctga aatactataa agatgtgatc gactcaacgt ataaaggcac gaaataa     1977

SEQ ID NO: 4            moltype = DNA   length = 1323
FEATURE                 Location/Qualifiers
source                  1..1323
                        mol_type = genomic DNA
                        note = Bhut Jolokia
                        organism = unidentified
SEQUENCE: 4
atggcgttcg cactgccgtc gagtctggtc tctgtgtgtg ataaatcctt catcaagccg     60
agttcgctga ccccgagcaa actgcgtttt cataaactga gcttcattga tcagtctctg    120
agtaatatgt atatcccgtg cgccttttc tacccgaaag tgcagcaacg tctggaagat    180
tctaagaaca gtgacgaact gtctcatatt gcacaccgtc cctgtcacaa                240
acgctggtta gctattaccc gtatgctggc aaaactgaagg ataacgcgac cgtggattgc    300
aatgacatgg gtgccgaatt tctgagcgtt cgcattaaat gttcgatgag cgaaatcctg    360
gatcatccgc acgcgtcgct ggccgaaagc attgtgctgc cgaaagacct gccgtgggct    420
aacaattgcg aaggcggtaa cctgctggtt gtgcaggtct cgaagtttga ttgcggcggt    480
attgcgatct ctgtgtgttt cagtcataaa atcggcgacg gttgtagcct gctgaacttt    540
ctgaatgatt ggagctctgt cacccgtgac cacaccacga ccgccctggt gccgtctccg    600
cgttttgtcg gtgattccgt gttctcaacc aaaaagtatg gttccctgat tacgccgcaa    660
atcctgtcag acctgaatga atgcgtgcaa aaacgtctga tcttcccgac cgataaactg    720
gacgcactgc gcgctaaggt ggcggaagaa tcgggcgtta aaaacccgac cgtggttca    780
gtcgtgagcg cgctgctgtt taaatgtgcc acgaaggcaa gttcctcaat gctgccgtcc    840
aagctggttc atttcctgaa tattcgcacc atgatcaaac cgcgtctgcc gcgcaacgcc    900
attggtaatc tgtcgagcat tttagcatc gaagcaacca atatgcagga tatggaactg    960
ccgacgctgg ttcgtaacct gcgcaaagaa gtggaagttg cgtacaaaaa ggatcaggtc   1020
gaacaaaacg aactgatcct ggaagttgtc gaatccatgc gtgaaggcaa actgccgttt   1080
gaaaacatgg atggttatga aaatgtgtac acctgctcaa acctgtgtaa atatccgtat   1140
tacacggttg acttcggctg gggtcgtccg gaacgcgtct gtctgggcaa cggtccgtct   1200
aagaacgcgt ttttcctgaa ggattacaag gccggcagg tgttgaagc acgtgtcatg   1260
ctgcacaaac agcaaatgag tgaatttgaa cgcaacgaag aactgctgga atttattgca   1320
taa                                                                  1323

SEQ ID NO: 5            moltype = DNA   length = 1464
FEATURE                 Location/Qualifiers
misc_feature            1..1464
                        note = Codon-optimized CaUGT2
```

```
source          1..1464
                mol_type = other DNA
                organism = synthetic construct
SEQUENCE: 5
atggttaatc aattacacat cttcaatttc ccgtttatgg cgcagggtca catgttaccg   60
gcgttggata tggcgaatct gttcacttca agaggcgtaa aagttacact gattaccact  120
catcaacacg tgccaatgtt tacgaagagc atcgaacgct cgcgtaattc tggtttcgat  180
atctcaatcc aaagcattaa attcccggcg agcgaagtag gcttacctga aggtatcgaa  240
tcattggatc aggttagcgg cgatgacgaa atgctgccga aattcatgcg cggtgttaac  300
ctgttacaac agccattaga acaattgctg caagaatcac gtccgcattg tttattgagc  360
gatatgtttt tcccttggac aacggaaagt gctgcaaaat tcggcattcc gcgcctgtta  420
tttcacggtt cttgctcatt cgctctgtcg gccgcgaat ctgtgcgtag aaataagcct  480
tttgaaaacg tctccaccga tactgaagaa tttgttgtgc cagacttgcc gcatcaaatt  540
aaactgacaa gaacgcagat cagtacctat gaacgcgaaa acatcgaatc cgatttcact  600
aagatgctga agaaagttcg tgacagcgaa agtacatcct acggtgtcgt agttaattct  660
ttctacgaat tagaaccaga ttacgcagac tattacatta acgttttggg ccgtaaagcc  720
tggcatatcg gtccgttttt gctgtgtaac aaactgcaag cagaagataa ggcccagaga  780
ggtaaaaagt cagcaattga tgccgacaa tgtctgaatt ggttagacag taaacaacct  840
aactccgtga tctatttgtg ctttggctcg atgcgaatc tgaactctgc tcaattgcac  900
gaaattgcta ctgcactgga atcttcaggc cagaatttca tctgggtggt cagaaaatgc  960
gtcgatgaag aaaacagcag taagtggttt cctgaaggtt tcgaagaacg caccaaagaa 1020
aagggcctga ttatcaaagg ttgggcacca cagactttaa ttttggaaca tgaatcggtg 1080
ggcgcctttg tcacacactg tggttggaac tctacgttgg aaggcatctg cgcgggtgta 1140
cctctggtta catggccatt tttcgctgaa caatttttca acgaaaaact gatcaccgaa 1200
gtattaaaga ctggttacgg cgttggtgcc cgtcagtgga gtagagtgtc cacggaaatt 1260
atcaaaggcg aagccattgc gaatgctatc aaccgcgtga tggtcggcga tgaagcagtc 1320
gaaatgagaa atcgcgccaa agacctgaaa gaaaaggcgc gtaaggcttt agaagaagat 1380
ggctcctcgt atagagactt gaccgcgctg attgaagaac tgggtgctta ccgctctcag 1440
gtggaacgta aacaacagga ttaa                                        1464

SEQ ID NO: 6         moltype = AA  length = 487
FEATURE              Location/Qualifiers
REGION               1..487
                     note = Codon-optimized CaUGT2
source               1..487
                     mol_type = protein
                     organism = synthetic construct
SEQUENCE: 6
MVNQLHIFNF PFMAQGHMLP ALDMANLFTS RGVKVTLITT HQHVPMFTKS IERSRNSGFD   60
ISIQSIKFPA SEVGLPEGIE SLDQVSGDDE MLPKFMRGVN LLQQPLEQLL QESRPHCLLS  120
DMFFPWTTES AAKFGIPRLL FHGSCSFALS AAESVRRNKP FENVSTDTEE FVVPDLPHQI  180
KLTRTQISTY ERENIESDFT KMLKKVRDSE STSYGVVVNS FYELEPDYAD YYINVLGRKA  240
WHIGPFLLCN KLQAEDKAQR GKKSAIDADE CLNWLDSKQP NSVIYLCFGS MANLNSAQLH  300
EIATALESSG QNFIWVVRKC VDEENSSKWF PEGFEERTKE KGLIIKGWAP QTLILEHESV  360
GAFVTHCGWN STLEGICAGV PLVTWPFFAE QFFNEKLITE VLKTGYGVGA RQWSRVSTEI  420
IKGEAIANAI NRVMVGDEAV EMRNRAKDLK EKARKALEED GSSYRDLTAL IEELGAYRSQ  480
VERKQD                                                            487
```

What is claimed is:

1. A biosynthetic method of making a glucoside of a capsaicinoid of interest comprising:
   a) expressing an acyl-CoA synthetase (ACS) and capsaicin synthase (CS) in a transformed cellular system;
   b) expressing a UDP-glucosyltransferase in the transformed cellular system, wherein the UDP-glucosyltransferase is a CaUGT2 from *C. roseus* and either is encoded by a DNA sequence at least 75% identical to SEQ ID NO: 5 and/or comprises an amino acid sequence at least 90% identical to SEQ ID NO: 6;
   c) growing the cellular system in a medium; and,
   d) producing the glucoside of a capsaicinoid of interest.

2. The biosynthetic method of claim 1, wherein both the ACS and CS are cloned from a plant of the *Capsicum* genus.

3. The biosynthetic method of claim 2, wherein the *Capsicum* genus plant is the ghost chili.

4. The biosynthetic method of claim 1, wherein the ACS expressed is derived from a gene cloned from *Arabidopsis* based on LCAS4 or LCAS5.

5. The biosynthetic method of claim 1, further comprising feeding a source material to said cellular system in addition to culture media.

6. The biosynthetic method of claim 5, wherein said source material is selected from the group consisting of nonanoic acid, oil of pelargonium, octanoic acid, and decanoic acid.

7. The biosynthetic method of claim 5, wherein said source material is selected from the group consisting of C6 to C12 hydrocarbons that are medium to long chain fatty acids.

8. The biosynthetic method of claim 5, wherein the transformed cellular system further comprises an aminotransferase which is capable of catalyzing the conversion of vanillin to vanillylamine, and the source material further comprises at least one of vanillin and vanillyamine.

9. The biosynthetic method of claim 1, wherein said transformed cellular system is selected from the group consisting of yeast, non-capsaicinoid producing plants, algae and bacteria.

10. The biosynthetic method of claim 9, wherein said transformed cellular system is *E.Coli*.

11. The biosynthetic method of claim 1, wherein the capsaicinoid of interest is selected from the group consisting of capsaicin, nonivamide, N-vanillylnonanamides, N-vanillylsulfonamides, N-vanillylureas, N-vanillylcarbamates, N[(substituted phenyl)methyl]alkylamides, methylene substituted N[(substituted phenyl)methyl]alkanamides, N[(substituted phenyl)methyll-cis-monosaturated alkenamides, N[(substituted phenyl)methyl]diunsaturated amides, 3-hydroxyacetanilide, hydroxyphenylacetamides, pseudocapsaicin, dihydrocapsaicin, nordihydrocapsaicin, homocapsaicin, homodihydrocapsaicin I, anandamide, piperine, zingerone, warburganal, polygodial, aframodial, cinnamodial, cinnamosmolide, cinnamolide, civamde, nonivamide, olvanil, N-oleylhomovanillamidia, isovelleral, scalaradial, ancistrodial, and any combinations or mixtures thereof.

12. The biosynthetic method of claim 1, wherein the capsaicinoid of interest is capsaicin or nonivamide.

13. The biosynthetic method of claim 1, wherein the ACS is encoded by a DNA sequence at least 75% identical to SEQ ID NO: 3.

14. The biosynthetic method of claim 1, wherein the ACS comprises an amino acid sequence at least 90% identical to SEQ ID NO: 1.

15. The biosynthetic method of claim 1, wherein the CS is encoded by a DNA sequence at least 75% identical to SEQ ID NO: 4.

16. The biosynthetic method of claim 1, wherein the CS comprises an amino acid sequence at least 90% identical to SEQ ID NO: 2.

17. The biosynthetic method of claim 1, wherein the ACS is encoded by a DNA sequence comprising the nucleotide sequence of SEQ ID NO: 3.

18. The biosynthetic method of claim 1, wherein the ACS comprises the amino acid sequence of sequence of SEQ ID NO: 1.

19. The biosynthetic method of claim 1, wherein the CS is encoded by a DNA comprising the nucleotide sequence of SEQ ID NO: 4.

20. The biosynthetic method of claim 1, wherein the CS comprises the amino acid sequence of SEQ ID NO: 2.

* * * * *